United States Patent
Augeri et al.

(10) Patent No.: US 10,729,671 B2
(45) Date of Patent: Aug. 4, 2020

(54) ZINC COMPLEXES OF HYDRAZONES AND (THIO)SEMICARBAZONES AND THEIR USE FOR THE TREATMENT OF CANCER

(71) Applicants: RUTGERS, THE STATE UNIVERSITY OF NEW JERSEY, New Brunswick, NJ (US); THE RESEARCH FOUNDATION FOR THE STATE UNIVERSITY OF NEW YORK, Syracuse, NY (US)

(72) Inventors: David J. Augeri, New Brunswick, NJ (US); Anthony F. Bencivenga, New Brunswick, NJ (US); Adam Blanden, Syracuse, NY (US); Darren R. Carpizo, New Brunswick, NJ (US); John A. Gilleran, New Brunswick, NJ (US); Spencer David Kimball, New Brunswick, NJ (US); Stewart N. Loh, Syracuse, NY (US); Xin Yu, New Brunswick, NJ (US)

(73) Assignees: Rutgers, the State University of New Jersey, New Brunswick, NJ (US); The Research Foundation for the State University of New York, Syracuse, NY (US)

( * ) Notice: Subject to any disclaimer, the term of this patent is extended or adjusted under 35 U.S.C. 154(b) by 0 days.

(21) Appl. No.: 15/545,975

(22) PCT Filed: Jan. 27, 2016

(86) PCT No.: PCT/US2016/015190
§ 371 (c)(1),
(2) Date: Jul. 24, 2017

(87) PCT Pub. No.: WO2016/123250
PCT Pub. Date: Aug. 4, 2016

(65) Prior Publication Data
US 2018/0000772 A1    Jan. 4, 2018

Related U.S. Application Data

(60) Provisional application No. 62/108,415, filed on Jan. 27, 2015, provisional application No. 62/258,261, filed on Nov. 20, 2015.

(51) Int. Cl.
| | | |
|---|---|---|
| *A61K 31/315* | (2006.01) |
| *A61K 31/443* | (2006.01) |
| *A61K 31/4439* | (2006.01) |
| *A61K 31/4436* | (2006.01) |
| *C07D 417/12* | (2006.01) |
| *C07D 413/12* | (2006.01) |
| *C07D 403/12* | (2006.01) |
| *C07D 277/82* | (2006.01) |
| *C07D 401/12* | (2006.01) |

(52) U.S. Cl.
CPC .......... *A61K 31/315* (2013.01); *A61K 31/443* (2013.01); *A61K 31/4436* (2013.01); *A61K 31/4439* (2013.01); *C07D 277/82* (2013.01); *C07D 401/12* (2013.01); *C07D 403/12* (2013.01); *C07D 413/12* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 4,665,173 A | 5/1987 | Klayman et al. |
| 7,112,680 B2 | 9/2006 | Hofmann et al. |
| 2008/0118576 A1 | 5/2008 | Theodorescu et al. |
| 2013/0345164 A1 | 12/2013 | Vazquez et al. |

(Continued)

FOREIGN PATENT DOCUMENTS

| | | |
|---|---|---|
| WO | 2001094340 A1 | 12/2001 |
| WO | 2006019955 A2 | 2/2006 |

(Continued)

OTHER PUBLICATIONS

Tian et al. disclose in Polyhedron 21, 1217-1222 (2002) (Year: 2002).*

(Continued)

*Primary Examiner* — Dennis Heyer
(74) *Attorney, Agent, or Firm* — Viksnins Harris Padys Malen LLP

(57) ABSTRACT

The invention provides complexes of Zn2+ of formulae (Ia) and (IIa) that are useful for treating cancer, as well as compositions and kits comprising such complexes.

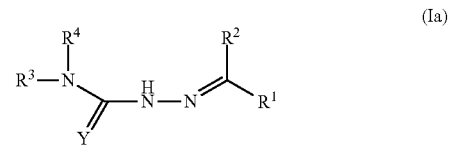

(Ia)

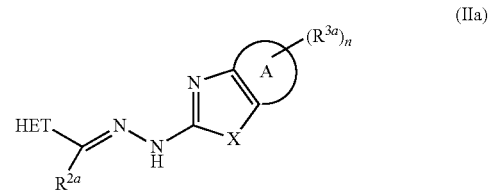

(IIa)

13 Claims, 2 Drawing Sheets

(56) References Cited

U.S. PATENT DOCUMENTS

| | | |
|---|---|---|
| 2014/0142266 A1 | 5/2014 | Sakamoto et al. |
| 2018/0000806 A1 | 1/2018 | Augeri et al. |
| 2018/0002279 A1 | 1/2018 | Augeri et al. |
| 2018/0002280 A1 | 1/2018 | Augeri et al. |

FOREIGN PATENT DOCUMENTS

| | | |
|---|---|---|
| WO | 2006101740 A2 | 9/2006 |
| WO | 2007035489 A2 | 3/2007 |
| WO | 2009039553 A1 | 4/2009 |
| WO | 2012175962 A1 | 12/2012 |
| WO | 2015021456 A1 | 2/2015 |
| WO | 2016123242 A1 | 8/2016 |
| WO | 2016123246 A1 | 8/2016 |
| WO | 2016123253 A1 | 8/2016 |

OTHER PUBLICATIONS

Heit et al. in Analytica Chimica Acta, 32, 448-455 (1965) (Year: 1965).*

Hall et al. in Arch. Pharm, Pharm, Med. Chem. 332, 115-123 (1999) (Year: 1999).*

Gudasi et al. In Transition Metal Chemistry 30:726-732 (2005) (Year: 2005).*

Rao et al. In Inorganic Chemistry, an Indian Journal 1(3), 47-52 (2006) (Year: 2006).*

Agrawal, et al., "Potential antitumor agents. 13. 4-Methyl-5-amino-1-formylisoquinoline thiosemicarbazone", Journal of Medicinal Chemistry 19(7), 970-972 (1976).

Antonini, et al., "Elucidation of the structure of the antineoplastic agents, 2-formylpyridine and 1-formylisoquinoline thiosemicarbazones", Journal of Medicinal Chemistry 20(3), 447-449 (1977).

Bellitto, et al., "Conformational Studies of Some Potentially Bidentate Thiosemicarba-zones and Related complexes of Zinc(II)", J.C.S. Dalton 68570(21), 758-762 (1976).

Chun-Ying, et al., "Synthesis, Crystal Structure and Nonlinear Optical Properties of Thiosemicarbazone Zinc Complex", J Coord Chem 47, 433-439 (1999).

Easmon, et al., "2-benzoxazolyl and 2-benzimidazolyl hydrazones derived from 2-acetylpyridine: a novel class of antitumor agents", Int J Cancer 94, 89-96 (2001).

Easmon, et al., "Synthesis, Structure—Activity Relationships, and Antitumor Studies of 2-Benzoxazolyl Hydrazones Derived from Alpha-(N)-acyl Heteroaromatics", J Med Chem 49, 6343-6350 (2006).

Easmon, et al., "Thiazolyl and benzothiazolyl hydrazones derived from α-(N)-acetylpyridines and diazines: synthesis, antiproliferative activity and CoMFA studies", Eur J Med Chem 32, 397-408 (1997).

File Caplus, "Preparation and characterization of vanillin thiosemicarbazone complexes with cobalt(II), nickel(II), copper(II), zinc(II), cadmium(II), and mercury(II)", STN CA Caesar Accession No. 1170, 2 pages (1984).

File Caplus, "Synthesis and crystal structure of zinc(II) complex [Zn(25-MBTSC)2I2]", STN CA Caesar Accession No. 1162, 1 page (2013).

File Caplus, "Synthesis and structure of 1.5Zn(phen)3.cntdot.L.cntdot..3N03 supramolecule (phen=o-phenanthroline, L=4-aminoacetophenone thiosemicarbazone", STN CA Caesar Accession No. 1176, 2 pages (2008).

Hall, et al., "Investigations on the Mechanism of Action of the Novel Antitumor Agents 2-Benzothiazolyl, 2-Benzoxazolyl, and 2-Benzimidazolyl Hydrazones Derived from 2-Acetylpyridine", Arch Pharm Pharm Med Chem 332 (4), 115-123 (1999).

Huang, et al., "A Series of α-Heterocyclic Carboxaldehyde Thiosemicarbazones Inhibit Topoisomerase IIα Catalytic Activity", Journal of Medicinal Chemistry 53, 3048-3064 (2010).

Huang, et al., "Correlating gene expression with chemical scaffolds of cytotoxic agents: ellipticines as substrates and inhibitors of MDR1", Pharmacogenomics Journal 5, 112-125 (2005).

Ibrahim, et al., "Indole-7-carbaldehyde thiosemicarbazone as a flexidentate ligand toward ZnII, CdII, PdII and PtII ions: cytotoxic and apoptosis-inducing properties of the PtII complex", Dalton Trans 43, 3860-3860 (2014).

Kalinowski, et al., "Design, Synthesis, and Characterization of Novel Iron Chelators: Structure—Activity Relationships of the 2-Benzoylpyridine Thiosemicarbazone Series and Their 3-Nitrobenzoyl Analogues as Potent Antitumor Agents", Journal of Medicinal Chemistry 50(15), 3716-3729 (2007).

Khalaji, et al., "Synthesis and Characterization of Zinc(II) Complexes with 3,4-Dimethoxybenzaldehyde Thiosemicarbazone: The Crystal Structure of [Zn(34-MBTSC) 2 Cl 2 ]", Phosphorus, Sulfur, and Silicon 188, 1119-1126 (2013).

Kovala-Demertzi, et al., "Zinc(II) complexes derived from pyridine-2-carbaldehyde thiosemicarbazone and (1E)-1-pyridin-2-ylethan-1-one thiosemicarbazone. Synthesis, crystal structures and antiproliferative activity of zinc(II) complexes", Journal of Inorganic Biochemistry 100, 1558-1567 (2006).

Mohan, et al., "Synthesis, Characterization, and Antitumor Properties of some Metal Complexes of 2,6-Diacetylpyridine Bis(N4-azacyclic Thiosemicarbazone)", Journal of Inorganic Biochemistry 34, 41-54 (1988).

Moorthy, et al., "QSAR analysis of 2-benzoxazolyl hydrazone derivatives for anticancer activity and its possible target prediction", Med Chem Res 21, 133-144 (2012).

Mrozek-Wilczkiewicz, et al., "Iron Chelators in Photodynamic Therapy Revisited: Synergistic Effect by Novel Highly Active Thiosemicarbazones", ACS Medicinal Chemistry Letters 5(4), 336-339 (2014).

Patent Cooperation Treaty, International Searching Authority, Search Report and Written Opinion for PCT/US2016/015190, 21 pages, dated Jun. 29, 2016.

Priyadharsini, et al., "Docking, synthesis, characterization and evaluation of novel cdk2 inhibitors: benzothiazole derivatives", International Journal of Pharmacy and Pharmaceutical Sciences 4(3), 574-585 (2012).

Ren, et al., "A new approach to suppress nonlinearity-transparency trade-off through coordination chemistry: syntheses and spectroscopic study on second-order nonlinear optical properties of a series of square-pyramidal zinc (II) complexes", Spectrochimica Acta Part A 59, 1095-1101 (2003).

Richardson, et al., "Dipyridyl Thiosemicarbazone Chelators with Potent and Selective Antitumor Activity Form Iron Complexes with Redox Activity", J Med Chem 49, 6510-6521 (2006).

Ruangpornvisuti, et al., "A DFT investigation of conformational geometries and interconversion equilibria of phenylthiosemicarbazone and its complexation with zinc", J Mol Model 10, 418-426 (2004).

Sleebs, et al., "Discovery of Potent and Selective Benzothiazole Hydrazone Inhibitors of Bcl-XL", J Med Chem 56, 5514-5540 (2013).

Todorovic, et al., "Synthesis and characterization of Zn(II) and Cd(II) complexes with 2,6-diacetylpyridine-bis (selenosemicarbazone). Crystal structure of a Ni(II) complex with a modified 2,6-diacetylpyridine-bis (selenosemicarbazone)", Inorganic Chemistry Communications 9, 862-865 (2006).

Webster, et al., "Synthesis and characterization of novel pentagonal bipyramidal compleses of iron(II), cobalt(II), and zinc(II)", Journal of American Chemical Society 95(19), 6505-6506 (1973).

Yu, et al., "Allele-Specific p53 Mutant Reactivation", Cancer Cell 21, 614-625 (2012).

Yu, et al., "Small molecule restoration of wildtype structure and function of mutant p53 using a novel zinc-metallochaperone based mechanism", Oncotarget 5(19), 8879-8892 (2014).

Vartale, et al., "Synthesis and Antimicrobial Activity of 6/7/8-Substituted-1-[ARYL/6' Substituted-2'-Benzothiazolyl]-Pyrazolo [4,5-b] Quinolines", Indian Journal of Heterocyclic Chemistry 16, 163-166 (2006).

(56) References Cited

OTHER PUBLICATIONS

Gudasi, K., et al., "Synthesis and spectral investigation of some transition metal complexes containing pentadentate acroacyclic NNNNN-donor Schiff base ligands", Transition Metal Chemistry 30, 726-732 (2005).
Bermejo, E., et al., "Complexes of Grup 12 Metals with 2-Acetylpyridine 4N-Dimethyl-thiosemiearbazone and with 2-Acetyipyridine-N-oxide 4N-Dimethyl-thiosemiearbazone: Synthesis, Structure and Antifungal Activity", Zeitschrift fuer Naturforschung, B: Chemical Sciences 54(6), 777-787 (1999).
Bjelogrlic, S., et al., "Synthesis, structure and characterization of novel Cd(II) and Zn(II) complexes with the aondensation product of 2-formylpyridine and selenosemicarbazide Antiproliferative activity of the synthesized complexes and related selenosemicarbazone complexes", Journal of Inorganic Biochemistry 104, 673-682 (2010).
Chhabra, N, et al., "A review of drug isomerism and its significance", Int J Appl Basic Med Res 3(1), 16-18 (2013).
Khaled, S., et al., "Synthesis and Spectroscopic Characterization of Some NOvel Polypyridine and Phenanthroline Complexes of Mn(II), Fe(II), Co(II) and Zn(II) Incorporating a Bidentate Benzothiazolyl Hydrazone Ligand", Chem Sci Trans 2(4), 1222-1231 (2013).
Kodela, R, et al., "Positional Isomers of Aspirin are Equally Potent in Inhibiting Colon Cancer Cell Growth: Differences in Mode of Cyclooxygenase Inhibition", J Pharmacol Exp Ther 346, 85-94 (2013).
Odashima, T, et al., "Determination of Microamounts of Iron by Extraction-Spectrophotometry with 2-Acetylpyridine-2-benzothiazolylhydrazone and Its Sensitization by Employing an Analog Derivative Technique", Microchemical Journal 33, 138-146 (1986).
Patani, George A., et al., "Bioisosterism: A Rational Approach in Drug Design", Chem Rev 96, 3147-3176 (1996).
Singh, K, et al., "Stereochemistry and Its Role in Drug Design", IJPSR 5(11), 4644-4659 (2014).
STN Record, Accession No. 1975:461709, JP49126728, 1 page (1975).

\* cited by examiner

ZINC COMPLEXES OF HYDRAZONES AND (THIO)SEMICARBAZONES AND THEIR USE FOR THE TREATMENT OF CANCER

CROSS-REFERENCE TO RELATED APPLICATIONS

This patent application claims the benefit of priority of U.S. application Ser. No. 62/108,415, filed Jan. 27, 2015, and of U.S. application Ser. No. 62/258,261, filed Nov. 20, 2015, which applications are herein incorporated by reference.

BACKGROUND OF THE INVENTION

TP53 is the most commonly mutated gene in human cancer for which no effective targeted anti-cancer drug exists. The majority of TP53 mutations (>70%) are missense mutations that generate a defective protein that is generally found at high levels in cancer cells due to loss of MDM2 negative feedback. Restoring the function of p53 in mouse models of cancer is highly therapeutic. Reactivating mutant p53 using small molecules has been highly sought after, yet remains an elusive goal in the development of cancer therapeutics.

SUMMARY OF THE INVENTION

This invention provides novel complexes, kits, and methods directed toward refolding TP53 mutant proteins into their wild-type conformations by treatment with zinc(II) metallo-chaperone complexes.

More specifically, one aspect of the present invention provides a complex comprising $Zn^{2+}$ and a compound of formula (Ia) or (IIa):

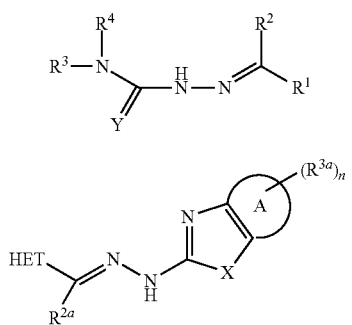

(Ia)

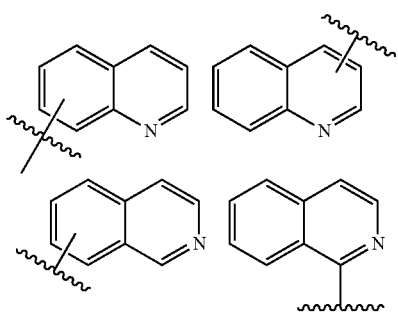

(IIa)

or an ion or poly-ion thereof, wherein:
the ring A is a fused benzo or heteroaryl ring;
$R^1$ is selected from the group consisting of:

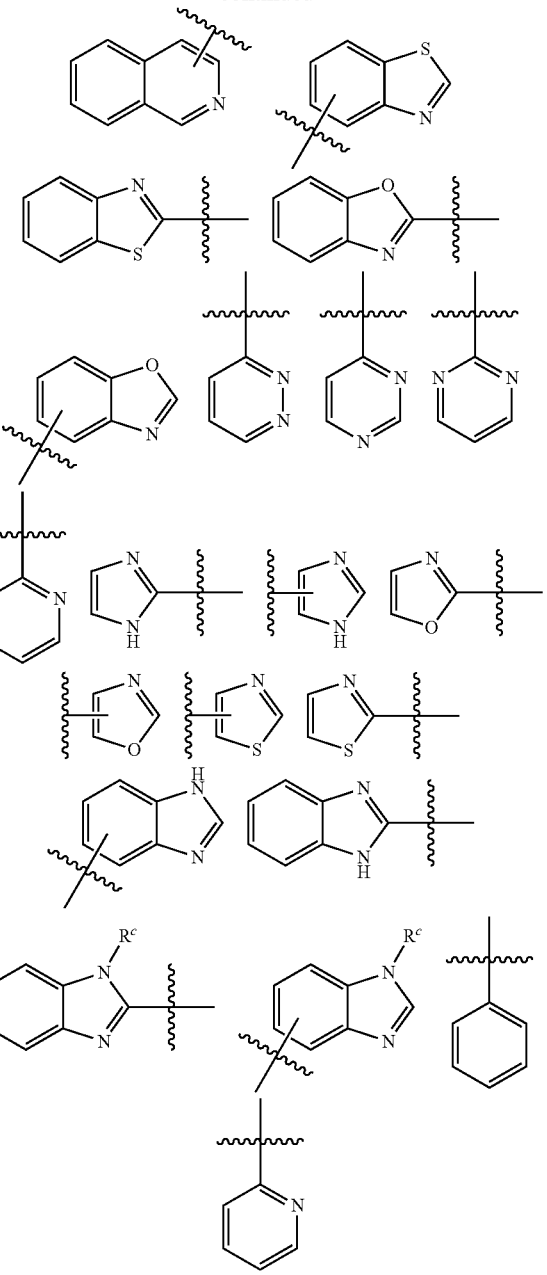

wherein $R^1$ is optionally substituted with one or more groups independently selected from halo, cyano, hydroxy, nitro, —$N(R^a)_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_1$-$C_6$)alkoxycarbonyl, ($C_2$-$C_6$)alkanoyloxy, ($C_4$-$C_6$)heterocycloalkyl, ($C_2$-$C_6$)alkylaminocarbonyl and ($C_2$-$C_6$)alkanoylamino wherein any phenyl, ($C_1$-$C_6$)alkyl, ($C_2$-$C_6$)alkenyl, ($C_2$-$C_6$)alkynyl, and ($C_3$-$C_6$)cycloalkyl, is optionally substituted with one or more groups independently selected from halo, cyano, hydroxy, nitro, —$N(R^a)_2$, carboxy, ($C_3$-$C_6$)cycloalkyl, ($C_1$-$C_6$)alkoxy, ($C_1$-$C_6$)alkanoyl, ($C_1$-$C_6$)alkoxycarbonyl, ($C_2$-$C_6$)alkanoyloxy, ($C_4$-$C_6$)heterocycloalkyl, ($C_2$-$C_6$)alkylaminocarbonyl and ($C_2$-$C_6$)alkanoylamino;
$R^2$ is selected from the group consisting of H, phenyl, heteroaryl, ($C_1$-$C_6$)alkyl, ($C_2$-$C_6$)alkenyl, ($C_2$-$C_6$)alkynyl, and (C₃-C₆)cycloalkyl, wherein any phenyl, heteroaryl, (C₁-C₆)alkyl, (C₂-C₆)alkenyl, (C₂-C₆)alkynyl, (C₃-C₆)cycloalkyl and C₄-C₆ heterocycloalkyl, is optionally substituted with one or more groups independently selected from halo, —N(R$^b$)₂, (C₃-C₆)cycloalkyl, (C₁-C₆)alkoxy, (C₂-C₆)alkanoyloxy, (C₂-C₆)alkoxycarbonyl, (C₂-C₆) alkylaminocarbonyl, and (C₂-C₆) alkanoylamino;

R³ and R⁴ are each independently selected from H, (C₁-C₆)alkyl, piperidinyl, or piperazinyl, which piperidinyl or piperazinyl is optionally substituted with pyridyl; or R³ and each R⁴ taken together with the nitrogen to which they are attached form a 3, 4, 5, 6, 7, 8, or 9 membered ring that is optionally substituted with one or more groups independently selected from the group consisting of halo;

Y is S, O, or Se;

each R$^a$ is independently selected from the group consisting of H, (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, wherein any (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, (C₂-C₆)alkoxycarbonyl, (C₂-C₆)alkylaminocarbonyl, and (C₂-C₆) alkanoylamino is optionally substituted with one or more groups independently selected from halo, (C₃-C₆)cycloalkyl, and (C₁-C₆)alkoxy; or two R$^a$ taken together with the nitrogen to which they are attached form a azetidino, pyrrolidino, piperidino, or morpholino ring;

each R$^b$ is independently selected from the group consisting of H, (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, wherein any (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, (C₂-C₆)alkoxycarbonyl, (C₂-C₆)alkylaminocarbonyl, and (C₂-C₆) alkanoylamino is optionally substituted with one or more groups independently selected from halo, (C₃-C₆)cycloalkyl, and (C₁-C₆)alkoxy; or two R$^b$ taken together with the nitrogen to which they are attached form a azetidino, pyrrolidino, piperidino, or morpholino ring;

R$^c$ is independently selected from the group consisting of H and (C₁-C₆)alkyl that is optionally substituted with one or more groups independently selected from halo, (C₃-C₆)cycloalkyl, and (C₁-C₆)alkoxy;

X is S, O, —CH=CH—, or N—R$^{aa}$;

HET is selected from the group consisting of:

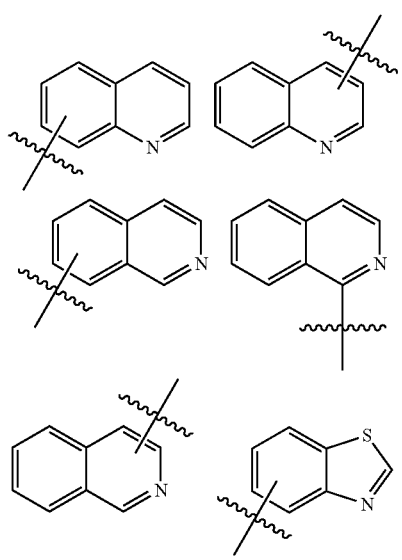

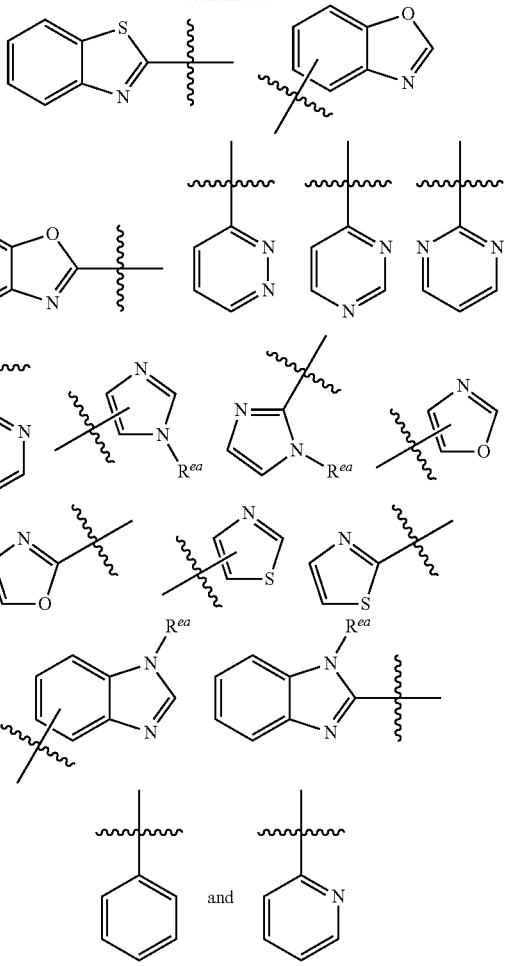

wherein HET is optionally substituted with one or more (e.g. 1, 2, 3, or 4) groups independently selected from halo, cyano, hydroxy, nitro, —N(R$^{aa}$)₂, carboxy, phenyl, (C₁-C₆)alkyl, (C₂-C₆)alkenyl, (C₂-C₆)alkynyl, (C₃-C₆)cycloalkyl, (C₁-C₆)alkoxy, (C₁-C₆)alkanoyl, (C₁-C₆)alkoxycarbonyl, (C₂-C₆)alkanoyloxy,

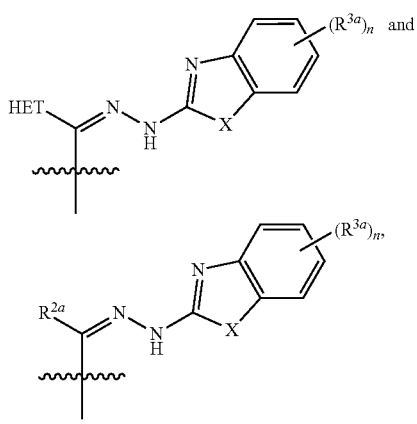

wherein any phenyl, (C₁-C₆)alkyl, (C₁-C₆)alkoxy, (C₂-C₆)alkenyl, (C₂-C₆)alkynyl, and (C₃-C₆)cycloalkyl, is optionally substituted with one or more groups independently selected from halo, azido, cyano, hydroxy, nitro, —N($R^{ba}$)$_2$, carboxy, ($C_3$-$C_6$)cycloalkyl, ($C_1$-$C_6$)alkanoyl, ($C_1$-$C_6$)alkoxycarbonyl, ($C_2$-$C_6$)alkanoyloxy, and ($C_1$-$C_6$)alkoxy that is optionally substituted with carboxy;

each $R^{2a}$ is independently selected from the group consisting of H, phenyl, ($C_1$-$C_6$)alkyl, ($C_2$-$C_6$)alkenyl, ($C_2$-$C_6$)alkynyl, and ($C_3$-$C_6$)cycloalkyl, wherein any phenyl, ($C_1$-$C_6$)alkyl, ($C_2$-$C_6$)alkenyl, ($C_2$-$C_6$)alkynyl, and ($C_3$-$C_6$)cycloalkyl, is optionally substituted with one or more groups independently selected from halo, —N($R^{Ca}$)$_2$, ($C_3$-$C_6$)cycloalkyl, ($C_1$-$C_6$)alkoxy, and ($C_2$-$C_6$)alkanoyloxy;

n is 0, 1, 2, 3, or 4;

each $R^{3a}$ is independently selected from halo, cyano, hydroxy, nitro, —N($R^{da}$)$_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_2$-$C_6$)alkoxycarbonyl, and ($C_2$-$C_6$)alkanoyloxy, wherein any phenyl, ($C_1$-$C_6$)alkyl, ($C_2$-$C_6$)alkenyl, ($C_2$-$C_6$)alkynyl, ($C_1$-$C_6$)alkoxy, and ($C_3$-$C_6$)cycloalkyl, is optionally substituted with one or more groups independently selected from halo, cyano, hydroxy, nitro, —N($R^c$)$_2$, carboxy, ($C_3$-$C_5$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy;

$R^{aa}$ is selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_5$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, —N($R^{ga}$)$_2$, morpholino, and ($C_1$-$C_6$)alkoxy; or two $R^{aa}$ taken together with the nitrogen to which they are attached form a azetidino, pyrrolidino, piperidino, or morpholino ring;

each $R^{ba}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, heteroaryl, and ($C_1$-$C_6$)alkoxy; or two $R^{ba}$ taken together with the nitrogen to which they are attached form a azetidino, pyrrolidino, piperidino, or morpholino ring; and each $R^{ca}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^{Ca}$ taken together with the nitrogen to which they are attached form a azetidino, pyrrolidino, piperidino, or morpholino ring;

each $R^{da}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^{da}$ taken together with the nitrogen to which they are attached form a azetidino, pyrrolidino, piperidino, or morpholino ring; or a solvate thereof;

$R^{ca}$ is independently selected from the group consisting of H and ($C_1$-$C_6$)alkyl that is optionally substituted with one or more groups independently selected from halo, ($C_3$-$C_6$)cycloalkyl, —N($R^{fa}$)$_2$, and ($C_1$-$C_6$)alkoxy;

each $R^{fa}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^{fa}$ taken together with the nitrogen to which they are attached form a azetidino, pyrrolidino, piperidino, or morpholino ring; and each $R^{ga}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^{ga}$ taken together with the nitrogen to which they are attached form a azetidino, pyrrolidino, piperidino, or morpholino ring;

provided that for a compound of formula (Ia), when $R^1$ is 2-pyridinyl, then $R^2$ is not H or ($C_1$-$C_6$)alkyl.

Another aspect of the present invention provides a method of inhibiting cancer cell growth comprising administering to a human afflicted with cancer, an amount of a complex having a $Zn^{2+}$ ion.

Another aspect of the present invention provides a method comprising:

combining $Zn^{2+}$ ions and a monomer in a ratio of 2:1 (monomer:zinc) to form a neutral complex; and diffusing the complex across a plasma membrane of a cell under conditions where the $Zn^{2+}$ ion will bind to a native ligation site of a mutant p53 inside the cell.

Another aspect of the present invention provides a method comprising: diffusing a charge neutral complex comprising a $Zn^{2+}$ ion across a plasma membrane of a cell under conditions where the $Zn^{2+}$ ion will bind to a native ligation site of a mutant p53 inside the cell.

Another aspect of the present invention provides a method comprising: contacting a cell having a mutant p53 with a charge neutral complex comprising a $Zn^{2+}$ ion under conditions where the complex enters the cell and induces a wild-type conformation change in the mutant p53.

Another aspect of the present invention provides a pharmaceutical composition comprising, in a pharmaceutically acceptable carrier, a compound to release zinc to p53.

Another aspect of the present invention provides a method of inhibiting cancer cell growth, comprising administering to an animal (e.g. a human), an effective amount of a compound or complex as described herein.

Another aspect of the present invention provides a method of inhibiting cancer cell growth, comprising administering to a human in need thereof, an effective amount of a complex as described herein and further comprising administering to the human a zinc supplement.

Another aspect of the present invention provides a method of inhibiting cancer cell growth comprising administering to a human afflicted with cancer, an amount of a neutral complex having a $Zn^{2+}$ ion, effective to inhibit growth of cancer cells in the human.

Another aspect of the present invention provides a method comprising: binding a $Zn^{2+}$ ion to a monomer in a ratio of 2:1 (monomer:zinc) to form a complex outside a cell; diffusing the complex including the $Zn^{2+}$ ion across a plasma membrane of the cell; and binding the $Zn^{2+}$ ion to a native ligation site of a mutant p53 inside the cell.

Another aspect of the present invention provides a method comprising: binding one or more zinc atoms in an extracellular environment of a cell having a mutant p53; and transporting the one or more zinc atoms into the cell to induce a wild-type conformation change in the mutant p53.

The invention further includes methods of preparing, methods of separating, and methods of purifying of the complexes described herein.

Additional advantages and novel features of this invention shall be set forth in part in the description that follows, and in part will become apparent to those skilled in the art upon examination of the following specification, or may be learned by the practice of the invention.

The advantages of the invention may be realized and attained by means of the instrumentalities, combinations, compositions, and methods particularly pointed out in the appended claims.

DESCRIPTION OF THE INVENTION

Figure 1:
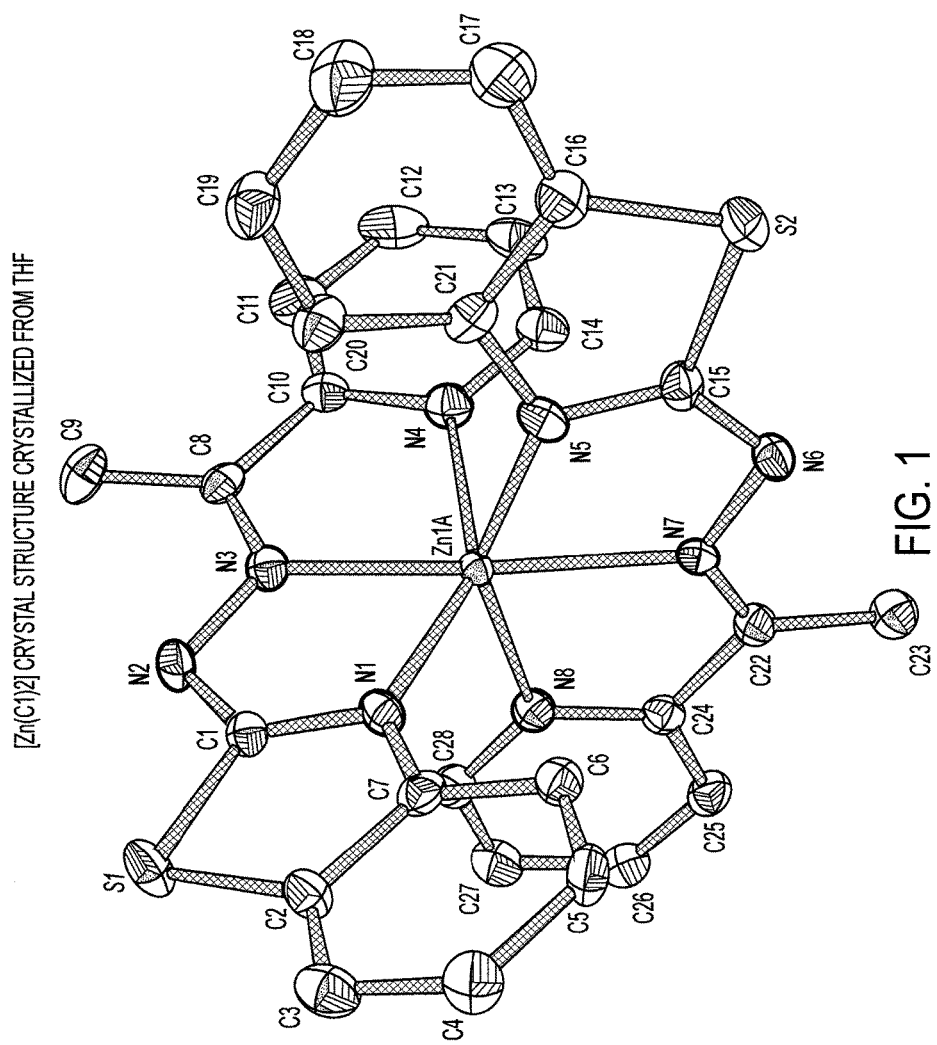
FIG. 1 shows the X-ray structure of compound 18 [Zn $(C_1)_2$]; ORTEP drawing from X-ray crystallographic data.

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term allyl as used herein refers to a substituent, molecular fragment, or radical having the chemical formula —$CH_2$—$CH$=$CH_2$.

The term "benzyl" as used herein refers to a substituent, molecular fragment, or radical having the chemical formula —$CH_2C_6H_5$.

The term "butyl" as used herein refers to a four-carbon alkyl radical, substituent, or molecular fragment having the chemical formula —$C_4H_9$.

The term "cyclopropyl" as used herein refers to a radical, substituent, or molecular fragment having a chemical structure derived from cyclopropane and having the chemical formula $C_3H_5$.

The term "ethyl" as used herein refers to an alkyl substituent, radical, or molecular fragment having the chemical formula —$C_2H_5$.

The term "isopropyl" as used herein refers to a propyl with a group attached to the secondary carbon.

The term "methyl" as used herein refers to an alkyl derived from methane and containing one carbon atom bonded to three hydrogen atoms and having the chemical formula —$CH_3$.

The term "propyl" as used herein refers to a linear three-carbon alkyl substituent, molecular fragment, or radical having the chemical formula —$C_3H_7$.

The term "phenyl" refers to a cyclic group of atoms, radical, substituent, or molecular fragment having the chemical formula —$C_6H_5$.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents.

Specifically, ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; and ($C_2$-$C_6$)alkanoyloxy can be acetoxy, propanoyloxy, butanoyloxy, isobutanoyloxy, pentanoyloxy, or hexanoyloxy.

In one specifically embodiment, each HET is independently selected from the group consisting of:

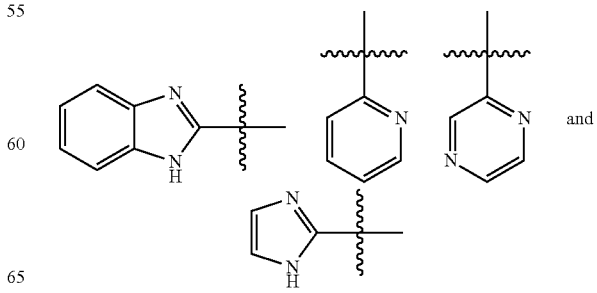

wherein HET is optionally substituted with one or more groups independently selected from halo, cyano, hydroxy, nitro, —N(R$^a$)$_2$, carboxy, phenyl, (C$_1$-C$_6$)alkyl, (C$_2$-C$_6$)alkenyl, (C$_2$-C$_6$)alkynyl, (C$_3$-C$_6$)cycloalkyl, (C$_1$-C$_6$)alkoxy, (C$_1$-C$_6$)alkanoyl, (C$_1$-C$_6$)alkoxycarbonyl, and (C$_2$-C$_6$)alkanoyloxy, wherein any phenyl, (C$_1$-C$_6$)alkyl, (C$_2$-C$_6$)alkenyl, (C$_2$-C$_6$)alkynyl, and (C$_3$-C$_6$)cycloalkyl, is optionally substituted with one or more groups independently selected from halo, cyano, hydroxy, nitro, —N(R$^a$)$_2$, carboxy, (C$_3$-C$_6$)cycloalkyl, (C$_1$-C$_6$)alkoxy, (C$_1$-C$_6$)alkanoyl, (C$_1$-C$_6$)alkoxycarbonyl, and (C$_2$-C$_6$)alkanoyloxy.

In one specifically embodiment, each HET is independently selected from the group consisting of:

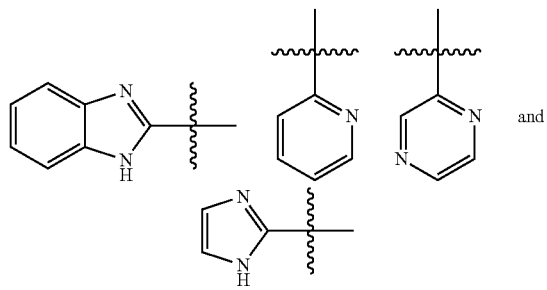

wherein HET is optionally substituted with one or more groups independently selected from (C$_1$-C$_6$)alkyl and —N(R$^a$)$_2$.

In one specifically embodiment, R$^2$ is selected from the group consisting of H, methyl, ethyl, propyl, isopropyl, butyl, tert-butyl, allyl, cyclopropyl, phenyl, benzyl, CH$_2$CH$_2$OCH$_3$, and CH$_2$CH$_2$—N(CH$_3$)$_2$.

In one specifically embodiment, R$^2$ is selected from the group consisting of methyl, ethyl, isopropyl, and tert-butyl.

The ability of ZMC1, NTA (Zn$^{2+}$-binding homolog), and A6 (structural homolog) to increase intracellular [Zn$^{2+}$]$_{free}$ was evaluated by treating cells with the fluorescent Zn$^{2+}$ indicator FluoZin-3-AM (FZ3-AM) in complete media and imaging them using confocal microscopy. In both HEK293 (non-cancer, p53-WT) and TOV112D (ovarian cancer, p53-R175H) cells, ZMC1 increased intracellular [Zn$^{2+}$]$_{free}$ as indicated by increased fluorescence, but NTA and A6 did not. This result is consistent with the metallochaperone (MC) model for ZMC1 function and explains the inability of NTA and A6 to reactivate p53-R175H at micromolar concentrations.

Of the two control compounds, A6 shuttled Zn$^{2+}$ into the liposomes, but NTA did not.

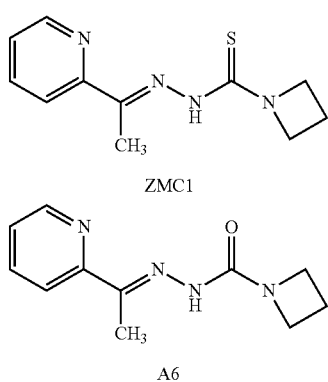

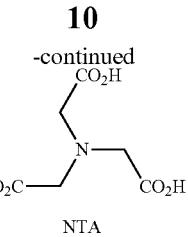

NTA binds Zn$^{2+}$ with an affinity similar to that of ZMC1, but it cannot cross either liposomal or cellular membranes, likely because it possesses negative charges. A6, on the other hand, lacks charges and is similar in structure to ZMC1, but binds Zn$^{2+}$ weakly (K$_d$=1.1 μM). It can function as an ionophore in conditions of the liposome experiments where external [Zn$^{2+}$]$_{free}$ was 10 μM. However, in complete media containing 10% fetal bovine serum (FBS), Zn$^{2+}$-binding proteins from the serum (e.g. albumin) necessarily compete for Zn$^{2+}$ with any putative MC, making the effective [Zn$^{2+}$]$_{free}$ much lower than [Zn$^{2+}$]$_{total}$. A6 therefore likely does not increase intracellular [Zn$^{2+}$]$_{free}$ in culture because K$_{d,A6}$ is greater than extracellular [Zn$^{2+}$]$_{free}$. Thus, both an appropriate Zn$^{2+}$ K$_d$ and ionophore activity influence ZMC1 activity.

To determine whether ZMC1 can traverse lipid bilayers as a free compound, the [Zn$^{2+}$]$_{free}$ gradient was reversed by adding a large excess of metal ion chelator EDTA to the solution outside of the liposomes; fluorescence was monitored in the presence and absence of ZMC1. EDTA alone did not cause a significant decrease in RZ-3 fluorescence as the liposomal membranes are impermeable to EDTA. After subsequent addition of ZMC1, there was a time dependent decrease in RZ-3 fluorescence. This result indicates that free ZMC1 crossed the liposomal membranes, bound internal Zn$^{2+}$, and transported it back outside the liposome where the metal was then bound by the much stronger chelator EDTA. Thus, ZMC1 can cross biological membranes both as free drug and drug-Zn$^{2+}$ complex, and therefore can transport Zn$^{2+}$ into cells without becoming trapped as either species.

To ensure that the fluorescence results were due to Zn$^{2+}$ transport and not to non-specific disruption of liposomal membranes, a liposomal leakage assay was performed using the self-quenching fluorophore calcein. When calcein is encapsulated at concentrations above 4 mM its fluorescence is decreased via self-quenching. Leakage is detected by a fluorescence increase as the dye dilutes and its fluorescence dequenches. At the highest concentrations of ZMC1 and ZnCl$_2$ a significant fluorescence increase was not detected. Disruption of liposomes can also be detected by alteration of their size distribution. The size distribution of liposomes treated with the highest concentrations of ZnCl$_2$ and ZMC1 was identical to that of untreated liposomes. Together, these data indicate the liposomal membranes remained intact upon ZMC1 treatment, and therefore the RZ-3 fluorescence changes are attributable only to specific Zn$^{2+}$ transport.

Characterization of ZMC1-Mediated Zn$^{2+}$ Transport in Live Cells

To extend the investigation of ZMC1 as an ionophore to living systems, ZMC1-mediated Zn$^{2+}$ transport was quantified in cells. The kinetics of intracellular [Zn$^{2+}$]$_{free}$ increase was measured by loading HEK293 and TOV112D cells with FZ3-AM, treating the cells with ZMC1 and ZnCl$_2$, and monitoring fluorescence by time-lapse microscopy. To minimize the potential for Zn$^{2+}$ contamination and contributions from poorly defined elements in complete media (e.g. FBS), cells were treated and imaged in Ca$^{2+}$ and Mg$^{2+}$-free Earle's Balanced Salt Solution supplemented with 10 mM HEPES pH 7.4 (EBSS/H (−)Ca/Mg). Excess ZnCl$_2$ with the Zn$^{2+}$ ionophore pyrithione (PYR) was used as a positive control. Excess membrane-permeable Zn$^{2+}$ chelator N,N,N',N'-tetrakis(2-pyridylmethyl)ethane-1,2-diamine (TPEN) was used as a negative control. When treated with ZnCl$_2$ alone or ZMC1 alone, neither cell type showed an increase in intracellular [Zn$^{2+}$]f,ee. When treated with both ZMC1 and ZnCl$_2$, both cell lines showed a time dependent increase at two different ZnCl$_2$ concentrations, demonstrating that both ZMC1 and extracellular Zn$^{2+}$ are required. When the fluorescence increases were fit to first-order exponentials, both concentrations of ZnCl$_2$ yielded identical half-lives in their respective cell types, which we combine to report $t_{1/2}$ (HEK293)=124±20 s and $t_{1/2}$ (TOV112D)=156±50 s (mean±SD, n=4).

The steady-state intracellular [Zn$^{2+}$]$_{free}$ of both cell types was then quantified after treatment with the 2:1 ratio of ZMC1:ZnCl$_2$. Cells were again loaded with FZ3-AM, treated with 1 μM ZMC1 and 0.5 μM ZnCl$_2$ in EBSS/H (−)Ca/Mg, and imaged as above. To normalize for differential dye loading, cells were then sequentially treated with excess PYR/ZnCl$_2$, imaged, treated with TPEN, and imaged again. PYR/ZnCl$_2$ and TPEN served to saturate and apoize the intracellular FZ3, respectively. In the absence of drug an intracellular [Zn$^{2+}$]$_{free}$ of 0.69±0.25 nM was measured for HEK293 cells and 0.71±0.19 nM was measured for TOV112D cells. These values reflect the lower limit of detection by FZ3-AM and are likely overestimates. Upon treatment with ZMC1 and ZnCl$_2$ intracellular [Zn$^{2+}$]$_{free}$ rose to 18.1±4.7 nM for HEK293 cells and 15.8±2.5 nM for TOV112D cells. These concentrations are theoretically sufficient to reactivate ~90% of p53-R175H based on the $K_{d1}$ value of 2.1 nM measured for DBD-R175H.

Materials and Methods
Reagents

FZ3-AM, RZ-3 (K$^+$ salt), and cell culture media were purchased from Life Technologies. DOPC was purchased from Avanti Polar Lipids. ZMC1 and A6 were similarly obtained. Zn$^{2+}$(ZMC1)$_2$ was synthesized and crystallized. HEK293 and TOV112D cells were purchased from ATCC and maintained in DMEM+GlutaMAX with 10% FBS and 1 mg/mL penicillin-streptomycin under a 5% CO$_2$ atmosphere at 37° C. All non-cell based experiments were conducted in 50 mM Tris pH 7.2, 0.1 M NaCl at 25° C.

Liposome Import Assay

DOPC-liposomes were prepared by film rehydration and extrusion followed by gel filtration and diluted to an OD$_{600}$=0.06 in buffer. The size distribution of the liposomes was determined by dynamic light scattering (DLS) using a Malvern Zetasizer Nano ZS. Fluorescence measurements were taken on a Horiba Fluoromax-4 spectrofluorimeter in a 5×5 mm quartz cuvette with $\lambda_{ex}/\lambda_{em}$=550/572 nm for RZ-3 and 490/515 nm for calcein. Initial Zn$^{2+}$ import/export was quantified by fitting the first 10-30 s of data after each treatment to a line and converted to units of flux using the following Eqn 1:

$$J_i = \frac{\Delta F}{\Delta t} \cdot \left(\frac{F_{max} - F_{min}}{[RZ3]}\right) \cdot \left(\frac{SA}{Vol}\right) \qquad \text{Eqn 1}$$

where $J_i$ is the initial flux, $\Delta F/\Delta t$ is the slope of the fit line, $F_{max}$ is RZ-3 fluorescence in the presence of saturating Zn$^{2+}$ and 1% TritonX-100, $F_{min}$ is RZ-3 fluorescence in the presence of excess EDTA and 1% TritonX-100, [RZ3] is the concentration of encapsulated RZ-3, and SA/Vol is the surface area to volume ratio calculated assuming hollow spheres of the mean diameter determined by DLS.

Intracellular [Zn$^{2+}$]$_{free}$ Imaging

TOV112D or HEK293 cells (40,000 cells/well) were plated on either 8-well BD Falcon chambered culture slides (Corning Life Sciences) or 8-chambered #1.5 Nunc Lab-Tek II chambered coverglasses (Thermo Scientific) treated with poly-L-lysine. After 48 h, cells were washed 2×5 m in serum-free media and incubated with 1 μM FZ3-AM for 40 m at 37° C. Cells were then washed 2×5 m in either EBSS/H (−)Ca/Mg or phenol-red free DMEM+10% FBS containing the indicated treatments for 20 m before imaging. For nuclear colocalization, 1 μg/mL Hoechst 33342 was also included. Cells were imaged using a Zeiss LSM510 META NLO confocal microscope equipped with 37° C. environmental control chamber. FZ3 and Hoechst 33342 were excited at 488 nm (argon laser) and 790 nm (Chameleon Ti:sapphire laser), respectively. To determine the kinetics of fluorescence change, each background-subtracted image in the time-lapse series was integrated in ImageJ and normalized to the integrated fluorescence of the first frame after treatment. For quantification of intracellular [Zn$^{2+}$]f,ee, each cell was analyzed in the treated, 50 μM PYR/ZnCl$_2$ (1:1), and 100 μM TPEN images by taking the mean fluorescence of an ROI inside the cell subtracted by an ROI immediately outside the cell measured in ImageJ. The [Zn$^{2+}$]$_{free}$ for each cell was then calculated by Eqn 2:

$$[Zn^{2+}]_{free} = \frac{F - F_{min}}{F_{max} - F} \cdot K_d \qquad \text{Eqn. 2}$$

Where F, $F_{max}$, and $F_{min}$ are fluorescence in the treatment, PYR/ZnCl$_2$, and TPEN images, respectively, and $K_d$ is that of FZ3 for Zn$^{2+}$ (15 nM) (31). To minimize the effects of outliers the lowest and highest 5% of cells in each series were rejected, and the remaining values averaged to give the value from that experiment. The number of cells analyzed in each trial ranged from 54-163. For nuclear colocalization, treated, PYR/ZnCl$_2$, and TPEN treated images costained with Hoechst 33342 were aligned and each pixel subjected to Eqn. 2 in MATLAB (MathWorks). The resultant images were Gaussian mean filtered and false-colored by calculated [Zn$^{2+}$]$_{free}$.

p53-R175H Immunofluorescence

DMEM+10% FBS was treated with 5 g Chelex 100 resin per 100 mL media for 1 hour with gentle shaking. The media was then decanted and filtered through 0.2 m sterile filter. TOV112D cells were then incubated with 1 μM ZMC1 in untreated media, Chelex-treated media, or media+10 μM TPEN at 37° C. for 2 h, fixed, and stained with PAB240 and PAB1640.

Assays:

Cell growth inhibition assay using human tumor cell lines with different p53 status (wildtype, null, p53-R175H) were employed to determine if wildtype structure is restored to mutant p53 after treatment with a zinc metallochaperone An immunofluorescence assay using conformation specific antibodies was used to determine if a test compound could induce a wildtype conformation of mutant p53.

The invention will now be illustrated by the following non-limiting Examples.

EXAMPLES

Chemistry: General Method A for the Synthesis of the [Zn(thiosemicarbazone)₂], [Zn(hydrazinylbenzo[d]thiazole)₂], [Zn(hydrazinylbenzo[d]oxazole)₂] and [Zn(hydrazinylbenzo[d]methylimidazole)₂] Complexes A general synthetic approach to the preparation small molecule complexes with $Zn^{+2}$ is shown in Scheme 1. Treatment of 3 with 0.5 equiv. of $ZnCl_2$ and excess triethylamine in ethanol heated to reflux for 2 hours afforded, after cooling to ambient temperature, the crystalline complex 18 (Kovala-Demertzi, D., Yadav, P. N., Wiecek, J., Skoulika, S., Varadinova, T., and Demertzis, M. A. (2006) Zn(II) complexes derived from pyridine-2-carbaldehyde thiosemicarbazone and (1E)-1-pyridin-2-ylethan-1-one thiosemicarbazone. Synthesis, crystal structures and antiproliferative activity of Zn(II) complexes. *Journal of Inorganic Biochemistry* 100, 1558-1567). Careful recrystallization from the appropriate solvent afforded crystals suitable for X-ray crystallographic analysis. In each case, the protocol gave the complex with 2:1 stoichiometry where two monomers were deprotonated to form a complex with Zn with an overall neutral charge. FIG. 1 shows the ORTEP drawing of the X-ray structure of compound 18.

Scheme 1

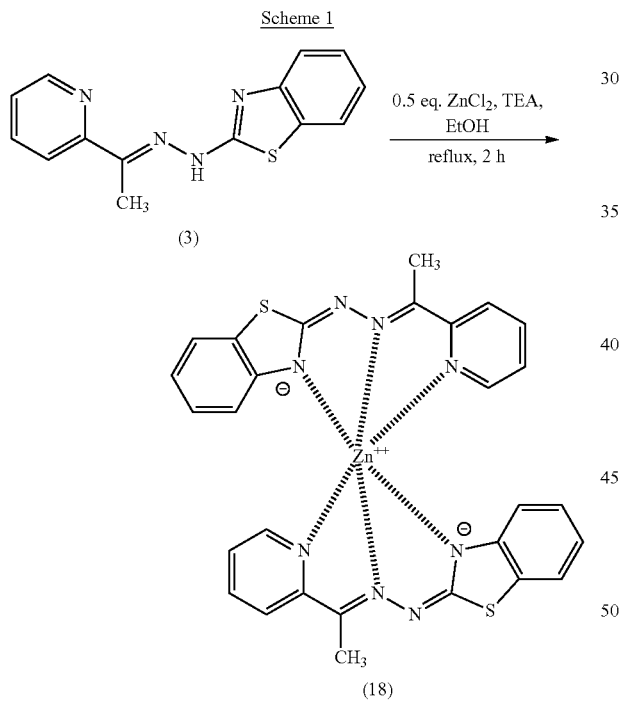

(18)

Example 1

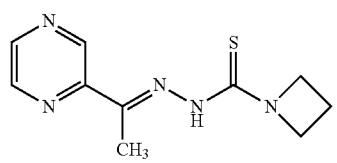 [SMILES: C/C(=N\NC(=S)N1CCC1)c1cnccn1]

(E)-N'-(1-(Pyrazin-2-yl)ethylidene)azetidine-1-carbothiohydrazide (1) General Method A To a solution of azetidine-1-carbothiohydrazide (156 mg, 1.19 mmol, 1.0 eq) and 1-(pyrazin-2-yl)ethan-1-one (152 mg, 1.25 mmol, 1.05 eq) in DCM (6 ml) was added AcOH (4 drops). After stirring overnight at room temperature, the reaction was concentrated under reduced pressure and recrystallized from MeOH to afford 1 as a crystalline white solid (132 mg, 0.56 mmol, 47%). ¹H-NMR (400 MHz, CDCl₃) δ 2.38 (t, J=7.72 Hz, 1H), 2.42 (t, J=7.88 Hz, 1H), 4.36 (br. t, J=7.52 Hz, 1H), 4.73 (br. t, J=7.40 Hz, 1H), 8.50 (d, J=2.56 Hz, 1H), 8.53 (m, 1H), 8.78 (s, 1H, NH), 9.13 (m, 1H). MS: 236.1 $[M+H]^+$.

Example 2

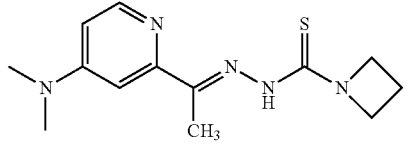 [SMILES: C/C(=N\NC(=S)N1CCC1)c1cc(N(C)C)ccn1]

(E)-N'-(1-(4-(dimethylamino)pyridin-2-yl)ethylidene)azetidine-1-carbothiohydrazide (2)

Following General Method A for the condensation of azetidine-1-carbothiohydrazide and 1-(4-(dimethylamino)pyridin-2-yl)ethan-1-one the title compound 2 was isolated as a white solid after recrystallization from MeOH. ¹H-NMR (400 MHz, CDCl₃) δ 2.34 (m, 5H), 3.02 (s, 6H), 4.34 (m, 2H), 4.70 (m, 2H), 6.49 and 6.54 (E/Z dd, J=6.04 Hz, 2.64 Hz, 1H), 6.62 and 7.08 (E/Z d, J=2.44 Hz, 1H), 8.26 (m, 1H), 8.71 (br. s, 1H, NH). MS: 278.0 $[M+H]^+$.

Example 3

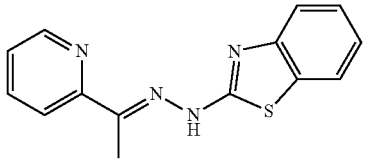

(E)-2-(2-(1-(pyridin-2-yl)ethylidene)hydrazinyl)benzo[d]thiazole (3)

Following General Method A for the condensation of 2-hydrazinylbenzo[d]thiazole and 1-(pyridin-2-yl)ethan-1-one the title compound 3 was isolated as a white solid after recrystallization from MeOH. ¹H-NMR (400 MHz, CDCl₃) δ 2.44 (s, 3H), 7.19 (dt, J=7.2 Hz, 1.01 Hz, 1H), 7.26 (m, 1H), 7.36 (dt, J=7.2 Hz, 1.01 Hz, 1H), 7.62 (d, J=7.96 Hz, 1H), 7.71 (d, J=7.08 Hz, 1H), 7.74 (dt, J=7.76 Hz, 1.76 Hz, 1H), 8.18 (d, J=8.12 Hz, 1H), 8.60 (br. d, J=4.32 Hz, 1H), 9.14 (br. s, 1H, NH). MS: 269.0 $[M+H]^+$.

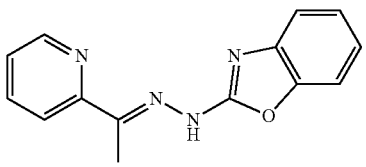 [SMILES: C/C(=N\Nc1nc2ccccc2o1)c1ccccn1]

Example 4

(E)-2-(2-(1-(pyridin-2-yl)ethylidene)hydrazinyl)benzo[d]oxazole (4)

Following General Method A for the condensation of 2-hydrazinylbenzo[d]oxazole and 1-(pyridin-2-yl)ethan-1-one the title compound 4 was isolated as a white solid after recrystallization from MeOH. $^1$H-NMR (400 MHz, CDCl$_3$) δ 2.48 (s, 3H), 7.16 (br. t, J=7.28 Hz, 1H), 7.28 (m, 2H), 7.44 (br. d, J=7.28 Hz, 1H), 7.51 (br. d, J=7.04 Hz), 7.73 (t, J=7.40 Hz, 1H), 8.27 (br. d, J=7.28 Hz, 1H), 8.60, (d, J=4.72 Hz, 1H), 8.85 (br. s, 1H, NH). MS: 253.1 [M+H]$^+$.

Example 5

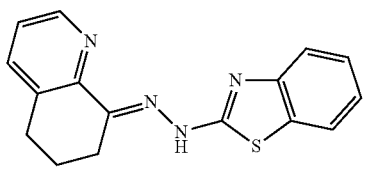 [SMILES: c1cnc2c(c1)CCC/C2=N\Nc1nc2ccccc2s1]

(E)-2-(2-(6,7-dihydroquinolin-8(5H)-ylidene)hydrazinyl)benzo[d]thiazole (5)

Following General Method A for the condensation of 2-hydrazinylbenzo[d]thiazole and 6,7-dihydroquinolin-8(5H)-one the title compound 5 was isolated as a white solid after recrystallization from MeOH. $^1$H-NMR (400 MHz, CDCl$_3$) δ 1.98 (m, 2H), 2.72 (br. t, J=6.48 Hz, 2H), 2.81 (br. t, J=5.88 Hz, 2H), 7.18 (m, 1H), 7.34 (t, J=7.40 Hz, 1H), 7.47 (d, J=7.44 Hz, 1H), 7.59 (d, J=7.92 Hz, 1H), 7.70 (d, J=7.72 Hz, 1H), 8.65 (d, J=3.92 Hz, 1H), 9.37 (br. s, 1H, NH). MS: 295.0 [M+H]$^+$.

Example 6

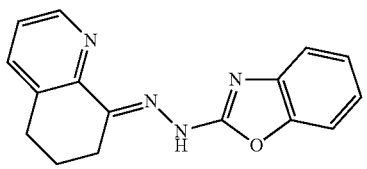 [SMILES: c1cnc2c(c1)CCC/C2=N\Nc1nc2ccccc2o1]

(E)-2-(2-(6,7-dihydroquinolin-8(5H)-ylidene)hydrazinyl)benzo[d]oxazole (6)

Following General Method A for the condensation of 2-hydrazinylbenzo[d]oxazole and 6,7-dihydroquinolin-8(5H)-one the title compound 6 was isolated as a white solid after recrystallization from MeOH. $^1$H-NMR (400 MHz, CDCl$_3$) δ 2.02 (m, 2H), 2.88 (t, J=6.00 Hz, 2H), 3.00 (br. t, J=5.64 Hz, 2H), 7.09 (m, 1H), 7.19 (m, 2H), 7.31 (m, 2H), 7.61 (d, J=7.60 Hz, 1H), 8.81 (br. s, 1H). MS: 279.1 [M+H]+.

Example 7

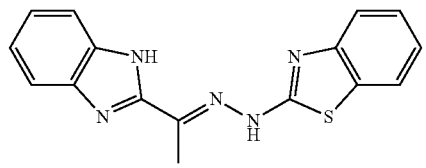 [SMILES: C/C(=N\Nc1nc2ccccc2s1)c1nc2ccccc2[nH]1]

(E)-2-((1-(1H-benzo[d]imidazol-2-yl)ethyl)diazenyl)benzo[d]thiazole (7)

Following General Method A for the condensation of 2-hydrazinylbenzo[d]thiazole and 1-(1H-benzo[d]imidazol-2-yl)ethan-1-one the title compound 7 was isolated as a white solid after recrystallization from MeOH. $^1$H-NMR (400 MHz, MeOD) δ 2.51 (s, 3H), 7.15 (t, J=7.60 Hz, 1H), 7.28 (m, 2H), 7.33 (t, J=7.28 Hz, 1H), 7.47 (s, 1H), 7.65 (m, 3H). MS: 308.1 [M+H]$^+$.

Example 8

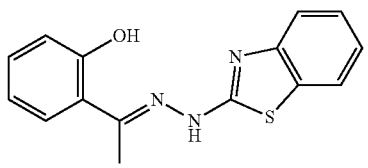 [SMILES: C/C(=N\Nc1nc2ccccc2s1)c1ccccc1O]

(E)-2-(1-(benzo[d]thiazol-2-yldiazenyl)ethyl)phenol (8)

Following General Method A for the condensation of 2-hydrazinylbenzo[d]thiazole and 1-(2-hydroxyphenyl)ethan-1-one the title compound 8 was isolated as a white solid after recrystallization from MeOH. $^1$H-NMR (400 MHz, CDCl$_3$) δ 2.49 (s, 3H), 6.91 (dt, J=8.04 Hz, 1.16 Hz, 1H), 7.04 (dd, J=8.20 Hz, 1.0 Hz, 1H), 7.13 (dt, J=7.72 Hz, 1.16 Hz, 1H), 7.25 (m, 1H), 7.30 (m, 2H), 7.52 (m, 2H), 12.42 (s, 1H, NH). MS: 284.0 [M+H]$^+$.

Example 9

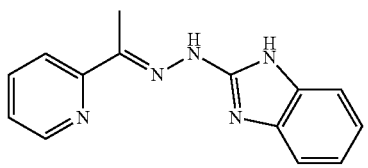 [SMILES: C/C(=N\Nc1nc2ccccc2[nH]1)c1ccccn1]

(E)-2-(2-(1-(pyridin-2-yl)ethylidene)hydrazinyl)-1H-benzo[d]imidazole (9)

Following General Method A for the condensation of 2-hydrazinyl-1H-benzo[d]imidazole and 1-(pyridin-2-yl)ethan-1-one the title compound 9 was isolated as a white solid after recrystallization from MeOH. $^1$H-NMR (400 MHz, CDCl$_3$) δ 2.44 (s, 3H), 7.14 (m, 2H), 7.26 (dt, J=6.92 Hz, 1.08 Hz, 1H), 7.40 (br. s, 2H), 7.72 (dt, J=7.64 Hz, 1.76 Hz, 1H), 8.08 (d, J=8.08 Hz, 1H), 8.60 (m, 1H). MS: 252.2 [M+H]$^+$.

Example 10

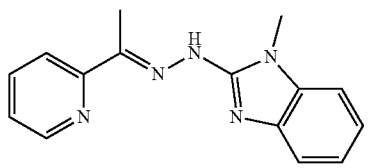

(E)-1-methyl-2-(2-(1-(pyridin-2-yl)ethylidene)hydrazinyl)-1H-benzo[d]imidazole (10)

Following General Method A for the condensation of 2-hydrazinyl-1-methyl-1H-benzo[d]imidazole and 1-(pyridin-2-yl)ethan-1-one the title compound 10 was isolated as a white solid after recrystallization from MeOH, $^1$H-NMR (400 MHz, CDCl$_3$) δ 2.59 (s, 3H), 3.54 (s, 3H), 7.02 (m, 4H), 7.21 (br. t, J=5.50 Hz, 1H), 7.67 (t, J=7.88 Hz, 1H), 8.08 (d, J=8.00 Hz, 1H), 8.60 (d, J=4.72 Hz, 1H), 9.10 (br. s, 1H, NH). MS: 266.3 [M+H]$^+$.

Example 11

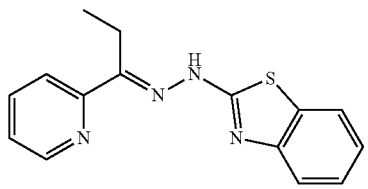 [SMILES: CC/C(=N\Nc1nc2ccccc2s1)c1ccccn1]

(E)-2-(2-(1-(pyridin-2-yl)propylidene)hydrazinyl)benzo[d]thiazole (11)

Following General Method A for the condensation of 2-hydrazinylbenzo[d]thiazole and 1-(pyridin-2-yl)propan-1-one the title compound 11 was isolated as a white solid after recrystallization from MeOH. $^1$H-NMR (400 MHz, CDCl$_3$) δ 1.21 (t, J=7.68 Hz, 3H), 2.99 (q, J=7.70 Hz, 2H), 7.19 (t, J=7.92 Hz, 1H), 7.26 (dt, J=5.92 Hz, 0.92 Hz, 1H), 7.36 (dt, J=8.16 Hz, 1.00 Hz, 1H), 7.62 (d, J=8.08 Hz, 1H), 7.71 (d, J=7.36 Hz, 1H), 7.73 (dt, J=7.64 Hz, 1.72 Hz, 1H), 8.16 (d, J=8.08 Hz, 1H), 8.59 (d, J=4.76 Hz, 1H), 9.11 (br. s, 1H, NH). MS: 283.2 [M+H]$^+$.

Example 12

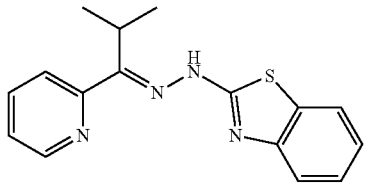 [SMILES: CC(C)/C(=N\Nc1nc2ccccc2s1)c1ccccn1]

(E)-2-(2-(2-methyl-1-(pyridin-2-yl)propylidene)hydrazinyl)benzo[d]thiazole (12)

Following General Method A for the condensation of 2-hydrazinylbenzo[d]thiazole and 2-methyl-1-(pyridin-2-yl)propan-1-one the title compound 12 was isolated as a white solid after recrystallization from MeOH. $^1$H-NMR (400 MHz, CDCl$_3$) δ 1.32 (s, 3H), 1.34 (s, 1H), 3.25 (m, 1H), 7.14 (dt, J=8.36 Hz, 1.04 Hz, 1H), 7.33 (m, 2H), 7.63 (dd, J=8.00 Hz, 2.40 Hz, 2H), 7.69 (d, J=7.80 Hz, 1H), 7.87 (dt, J=8.04 Hz, 1.84 Hz, 1H), 8.73 (d, J=4.38 Hz, 1H), 14.86 (br. s, 1H). MS: 297.3 [M+H]$^+$.

Example 13

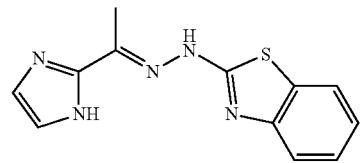 [SMILES: C/C(=N\Nc1nc2ccccc2s1)c1ncc[nH]1]

(E)-2-(2-(1-(1H-imidazol-2-yl)ethylidene)hydrazinyl)benzo[d]thiazole (13)

Following General Method A for the condensation of 2-hydrazinylbenzo[d]thiazole and 1-(1H-imidazol-2-yl)ethan-1-one the title compound 13 was isolated as a white solid after recrystallization from MeOH. $^1$H-NMR (400 MHz, CDCl$_3$) δ 2.42 (s, 3H), 7.17 (m, 3H), 7.34 (t, J=7.36 Hz, 1H), 7.53 (d, J=7.92 Hz, 1H), 7.66 (d, J=7.84 Hz, 1H), 9.89 (br. s, 1H, NH). MS: 258.2 [M+H]$^+$.

Example 14

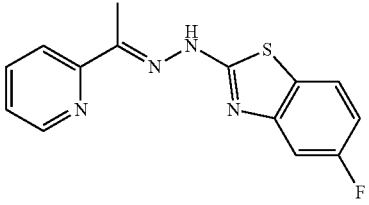 [SMILES: C/C(=N\Nc1nc2cc(F)ccc2s1)c1ccccn1]

(E)-5-fluoro-2-(2-(1-(pyridin-2-yl)ethylidene)hydrazinyl)benzo[d]thiazole (14)

Following General Method A for the condensation of 5-fluoro-2-hydrazinylbenzo[d]thiazole and 1-(pyridin-2-yl)

ethan-1-one the title compound 14 was isolated as a white solid after recrystallization from MeOH. $^1$H-NMR (400 MHz, CDCl$_3$) δ 2.45 (s, 3H), 6.94 (dt, J=8.80 Hz, 2.48 Hz, 1H), 7.28 (ddd, J=5.88 Hz, 4.92 Hz, 0.92 Hz, 1H), 7.32 (dd, J=9.76 Hz, 2.44 Hz, 1H), 7.61 (dd, J=8.64 Hz, 5.20 Hz, 1H), 7.74 (dt, J=7.64 Hz, 1.72 Hz, 1H), 8.16 (d, J=8.08 Hz, 1H), 8.60 (d, J=4.80 Hz, 1H), 9.00 (br. s, 1H, NH). MS: 287.0 [M+H]+.

Example 15

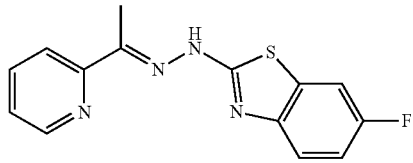 [SMILES: C/C(=N\Nc1nc2ccc(F)cc2s1)c1ccccn1]

(E)-6-fluoro-2-(2-(1-(pyridin-2-yl)ethylidene)hydrazinyl)benzo[d]thiazole (15)

Following General Method A for the condensation of 6-fluoro-2-hydrazinylbenzo[d]thiazole and 1-(pyridin-2-yl)ethan-1-one the title compound 15 was isolated as a white solid after recrystallization from MeOH. $^1$H-NMR (400 MHz, CDCl$_3$) δ 2.44 (s, 3H), 7.09 (dt, J=8.92 Hz, 2.60 Hz, 1H), 7.27 (ddd, J=6.00 Hz, 4.92 Hz, 1.12 Hz, 1H), 7.41 (dd, J=8.16 Hz, 2.60 Hz, 1H), 7.55 (dd, J=8.84 Hz, 4.68 Hz, 1H), 7.74 (dt, J=7.60 Hz, 1.80 Hz, 1H), 8.15 (d, J=8.08 Hz, 1H), 8.60 (app. d, J=4.80 Hz, 1H), 8.97 (br. s, 1H, NH). MS: 355.2 [M+H]$^+$.

Example 16

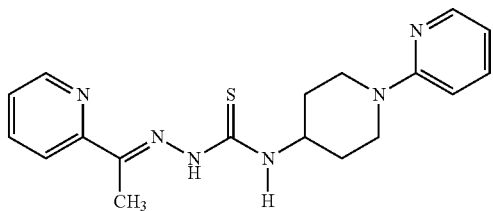 [SMILES: C/C(=N\NC(=S)NC1CCN(c2ccccn2)CC1)c1ccccn1]

(E)-2-(1-(pyridin-2-yl)ethylidene)-N-(1-(pyridin-2-yl) piperidin-4-yl)hydrazine-1-carbothioamide (16)

Following General Method A for the condensation of N-(1-(pyridin-2-yl)piperidin-4-yl)hydrazinecarbothioamide and 1-(pyridin-2-yl)ethan-1-one the title compound 16 was isolated as a white solid after recrystallization from MeOH. $^1$H-NMR (400 MHz, CDCl$_3$) δ 1.76 (ddd, J=15.33 Hz, 11.72 Hz, 3.92 Hz, 2H), 2.30 (m, 2H), 2.42 (s, 3H), 3.04 (dt, J=13.73 Hz, 2.40 Hz, 2H), 3.72 (m, 2H), 4.57 (m, 1H), 7.16 and 7.19 (E/Z d, 1.56 Hz, 1H), 7.21 and 7.24 (E/Z m, 1H), 7.30 (ddd, J=5.87 Hz, 4.92 Hz, 1.04 Hz), 7.52 (br. d, J=8.16 Hz, 1H, NH), 7.72 (dt, J=7.76 Hz, 1.72 Hz, 1H), 7.90 (d, J=8.04 Hz, 1H), 8.11 (dd, J=4.44 Hz, 1.32 Hz, 1H), 8.35 (d, J=2.68 Hz, 1H), 8.61 (d, J=4.12 Hz, 1H), 8.68 (br. s, 1H, NH). MS: 287.0 [M+H]$^+$.

Example 17

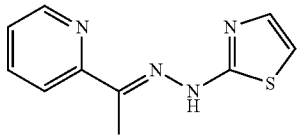

(E)-2-(2-(1-(pyridin-2-yl)ethylidene)hydrazinyl)thiazole (17)

To a solution of (E)-2-(1-(pyridin-2-yl)ethylidene)hydrazine-1-carbothioamide (6) (100 mg, 0.52 mmol, 1 eq) in DMF (0.75 ml) was added chloroacetaldehyde (50% wt. in H$_2$O, 65.4 µL, 0.52 mmol, 1 eq), and KOAc (50.5 mg, 0.52 mmol, 1 eq). The reaction was stirred overnight at 60 C and diluted in H$_2$O (20 ml) to crash out crude product. The solid was partitioned in DCM/H$_2$O and extracted 2×DCM. The combined organics were dried over Na$_2$SO$_4$, filtered, concentrated and purified by silica gel chromatography (eluting in 20% to 50% EtOAc/Hex). The combined product containing fractions were concentrated and recrystallized from MeOH to afford 17 as a white solid. $^1$H-NMR (400 MHz, CDCl$_3$) δ 2.44 (s, 3H), 6.71 (d, J=3.60 Hz, 1H), 7.23 (ddd, J=5.96 Hz, 4.88 Hz, 1.04 Hz, 1H), 7.30 (d, J=3.64 Hz, 1H), 7.70 (dt, J=7.84 Hz, 1.76 Hz, 1H), 8.15 (d, J=8.08 Hz, 1H), 8.57 (app. d, J=4.46 Hz, 1H). MS: 218.9 [M+H]$^+$.

Example 18

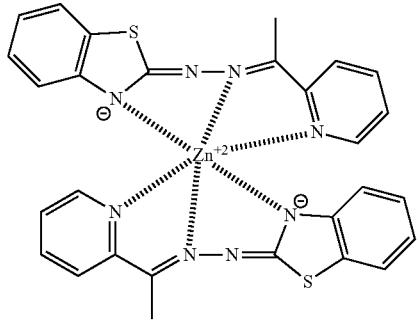

Synthesis of (18)

Figure 2:
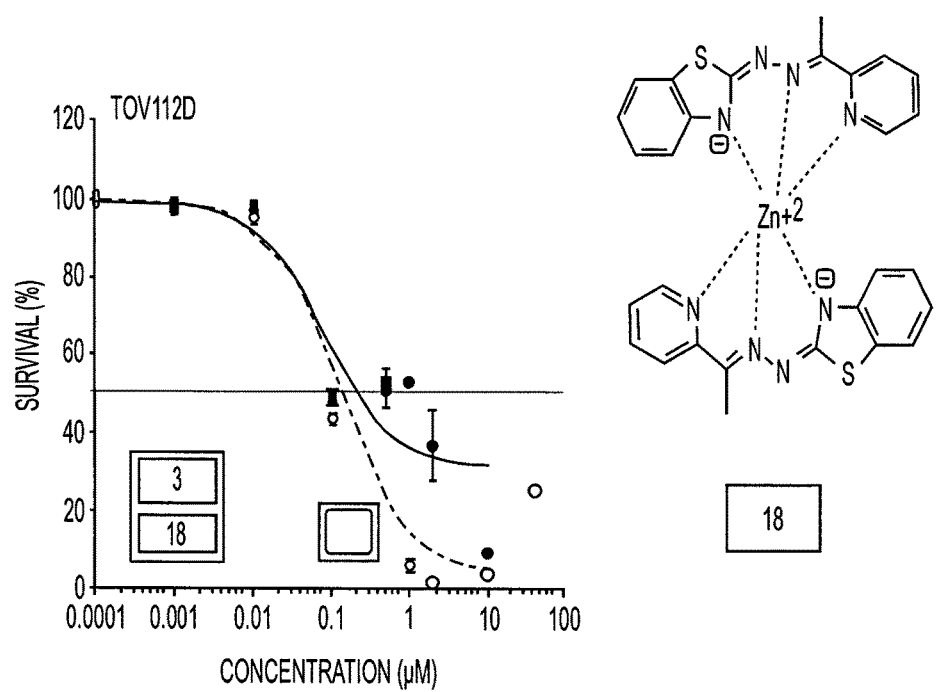
FIG. 2 illustrates the potency of Zn (II) complex 18.

To a suspension of 10 (75.0 mg, 0.279 mmol, 1 equiv.) in EtOH (7 ml) was added ZnCl$_2$ (19.1 mg, 0.140 mmol, 0.5 equiv.). After 5 minutes, TEA (0.279 ml, excess) was added and the mixture was heated for 2 hours at reflux under nitrogen. Upon cooling to ambient temperature, a solid precipitated that was collected by filtration and washed with 1:1 EtOH/water mixture followed by Et$_2$O. The solids were dried under high vacuum to give [Zn(Cl)$_2$] 18, (64.6 mg, 0.108 mmol, 77%) as an orange solid. H-NMR (400 MHz, DMSO-d$_6$) δ 2.66 (s, 6H), 6.64 (d, J=7.96 Hz, 2H), 6.78 (t, J=Hz, Hz, 2H), 6.97 (t, J=Hz, Hz, 2H), 7.29 (t, J=Hz, Hz, 2H), 7.48 (d, J=7.76 Hz, 2H), 7.85 (m, 2H), 7.91 (m, 4H). Slow evaporation of [Zn(Cl)$_2$] from THF afforded orange crystals that were suitable for X-ray crystallography. See X-ray ORTEP drawing (FIG. 2) and data tables.

Example 19
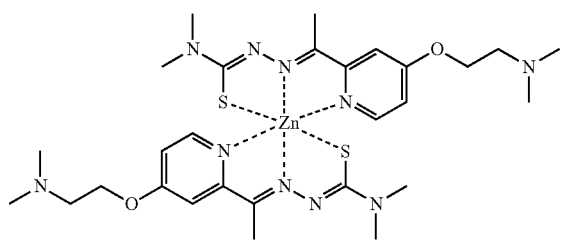
Synthesis of (19)
The title compound was prepared using Method A. $^1$H NMR (500 MHz, Methanol-$d_4$) δ 7.69 (dd, J=5.9, 0.8 Hz, 1H), 7.22 (d, J=2.4 Hz, 1H), 6.76 (ddd, J=5.9, 2.4, 0.8 Hz, 1H), 4.19 (t, J=5.4 Hz, 2H), 3.30 (d, J=0.8 Hz, 6H), 2.77 (t, J=5.4 Hz, 2H), 2.59 (d, J=0.8 Hz, 3H), 2.32 (d, J=0.8 Hz, 6H). (MS+H)+ 310.30 (monomer mass)
Cell-based TOV112D activity for representative compounds is shown in Table 1.
TABLE 1
| COMPOUND Number | Structure | Activity TOV112D |
|---|---|---|
| 1 | | ++ |
| 2 | | +++ |
| 3 | | +++ |
| 4 | | +++ |
| 7 | | ND |
| 8 | 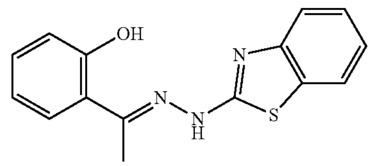 [SMILES: C/C(=N\Nc1nc2ccccc2s1)c1ccccc1O] | ND |
| 9 | 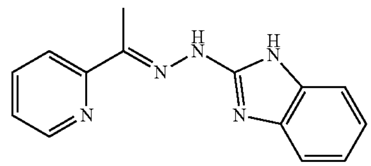 [SMILES: C/C(=N\Nc1nc2ccccc2[nH]1)c1ccccn1] | +++ |
| 10 | 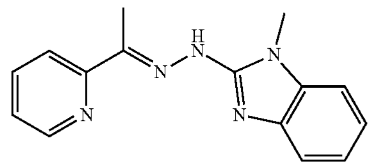 [SMILES: C/C(=N\Nc1nc2ccccc2n1C)c1ccccn1] | +++ |
| 11 | 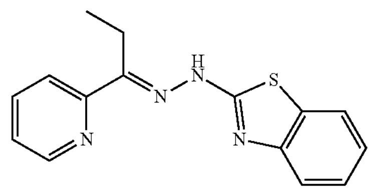 [SMILES: CC/C(=N\Nc1nc2ccccc2s1)c1ccccn1] | +++ |
| 12 | 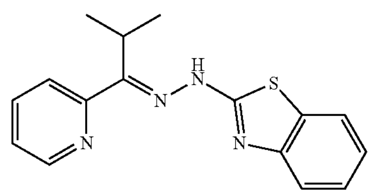 [SMILES: CC(C)/C(=N\Nc1nc2ccccc2s1)c1ccccn1] | + |
| 13 | 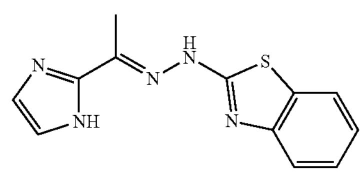 [SMILES: C/C(=N\Nc1nc2ccccc2s1)c1ncc[nH]1] | + |
| 14 | 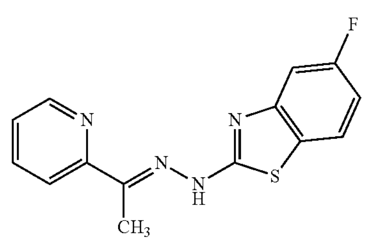 [SMILES: C/C(=N\Nc1nc2cc(F)ccc2s1)c1ccccn1] | +++ |
| 15 | 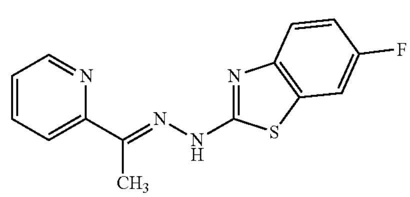 [SMILES: C/C(=N\Nc1nc2ccc(F)cc2s1)c1ccccn1] | +++ |

TABLE 1-continued

| COMPOUND Number | Structure | Activity TOV112D |
|---|---|---|
| 18 | 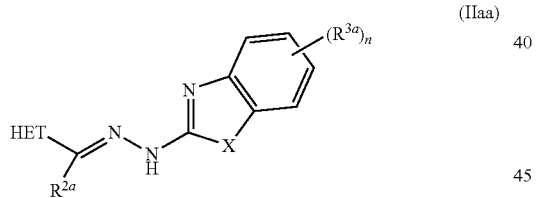 | +++ |

+++, most active;
++, moderately active;
+, less active

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A complex comprising $Zn^{2+}$ and a compound of formula (IIaa):

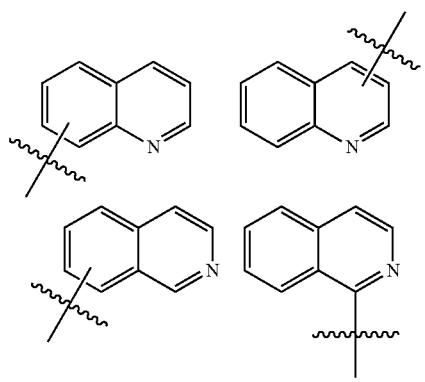

(IIaa)

or a solvate, ion or poly-ion thereof, wherein:
X is S, O, —CH=CH—, or N—$R^{aa}$;
HET is selected from the group consisting of:

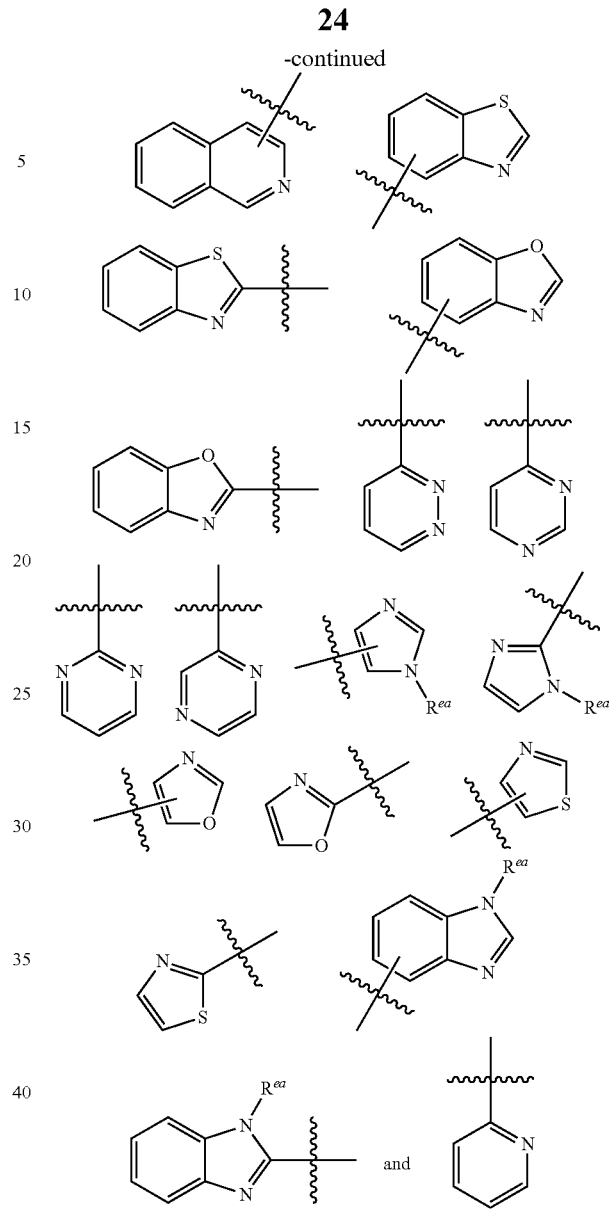

wherein HET is optionally substituted with one or more groups independently selected from halo, cyano, hydroxy, nitro, —N($R^{aa}$)$_2$, carboxy, phenyl, ($C_1$-$C_6$) alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_1$-$C_6$) alkoxycarbonyl, ($C_2$-$C_6$)alkanoyloxy,

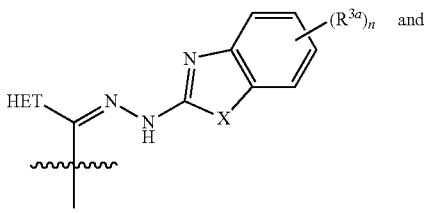 and wherein any phenyl, ($C_1$-$C_6$)alkyl, ($C_1$-$C_6$)alkoxy, ($C_{2-6}$) alkenyl, ($C_{2-6}$)alkynyl, and ($C_3$-$C_6$)cycloalkyl, is optionally substituted with one or more groups independently selected from halo, azido, cyano, hydroxy, nitro, —N($R^{ba}$)$_2$, carboxy, ($C_3$-$C_6$)cycloalkyl, ($C_1$-$C_6$)alkanoyl, ($C_1$-$C_6$)alkoxycarbonyl, ($C_2$-$C_6$)alkanoyloxy, and ($C_1$-$C_6$)alkoxy that is optionally substituted with carboxy;

each $R^{2a}$ is independently selected from the group consisting of phenyl, ($C_1$-$C_6$)alkyl, ($C_2$-$C_6$)alkenyl, ($C_2$-$C_6$)alkynyl, and ($C_3$-$C_6$)cycloalkyl, wherein any phenyl, ($C_1$-$C_6$)alkyl, ($C_2$-$C_6$)alkenyl, ($C_2$-$C_6$)alkynyl, and ($C_3$-$C_6$)cycloalkyl, is optionally substituted with one or more groups independently selected from halo, —N($R^{ca}$)$_2$, ($C_3$-$C_6$)cycloalkyl, ($C_1$-$C_6$)alkoxy, and ($C_2$-$C_6$)alkanoyloxy;

n is 0, 1, 2, 3, or 4;

each $R^{3a}$ is independently selected from halo, cyano, hydroxy, nitro, —N($R^{da}$)$_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy, wherein any phenyl, ($C_1$-$C_6$)alkyl, ($C_2$-$C_6$)alkenyl, ($C_2$-$C_6$)alkynyl, ($C_1$-$C_6$)alkoxy, and ($C_3$-$C_6$)cycloalkyl, is optionally substituted with one or more groups independently selected from halo, cyano, hydroxy, nitro, —N($R^c$)$_2$, carboxy, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy;

$R^{aa}$ is selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, —N($R^{ga}$)$_2$, morpholino, and ($C_1$-$C_6$)alkoxy; or two $R^{aa}$ taken together with the nitrogen to which they are attached form a azetidino, pyrrolidino, piperidino, or morpholino ring;

each $R^{ba}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, heteroaryl, and ($C_1$-$C_6$)alkoxy; or two $R^{ba}$ taken together with the nitrogen to which they are attached form a azetidino, pyrrolidino, piperidino, or morpholino ring; and each $R^{ca}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^{ca}$ taken together with the nitrogen to which they are attached form a azetidino, pyrrolidino, piperidino, or morpholino ring;

each $R^{da}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^{da}$ taken together with the nitrogen to which they are attached form a azetidino, pyrrolidino, piperidino, or morpholino ring; or a solvate thereof;

$R^{ea}$ is independently selected from the group consisting of H and ($C_1$-$C_6$)alkyl that is optionally substituted with one or more groups independently selected from halo, ($C_3$-$C_6$)cycloalkyl, —N($R^{fa}$)$_2$, and ($C_1$-$C_6$)alkoxy;

each $R^{fa}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^{fa}$ taken together with the nitrogen to which they are attached form a azetidino, pyrrolidino, piperidino, or morpholino ring; and each $R^{ga}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^{ga}$ taken together with the nitrogen to which they are attached form a azetidino, pyrrolidino, piperidino, or morpholino ring; provided the compound is not

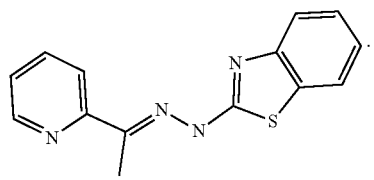 [SMILES: C/C(=N\Nc1nc2ccccc2s1)c1ccccn1 ; "."]

2. The complex of claim 1 or a solvate, ion or poly-ion thereof, wherein:
X is S, O, or N—$R^{aa}$; and
HET is optionally substituted with one or more groups independently selected from halo, cyano, hydroxy, nitro, —N($R^{aa}$)$_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_1$-$C_6$)alkoxycarbonyl, ($C_2$-$C_6$)alkanoyloxy, and

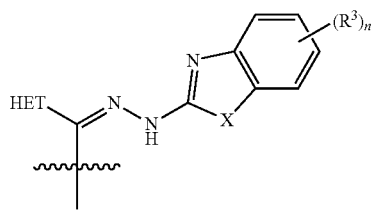

wherein any phenyl, $(C_1\text{-}C_6)$alkyl, $(C_1\text{-}C_6)$alkoxy, $(C_2\text{-}C_6)$alkenyl, $(C_2\text{-}C_6)$alkynyl, and $(C_3\text{-}C_6)$cycloalkyl, is optionally substituted with one or more groups independently selected from halo, cyano, hydroxy, nitro, $-N(R^{ba})_2$, carboxy, $(C_3\text{-}C_6)$cycloalkyl, $(C_1\text{-}C_6)$alkoxy, $(C_1\text{-}C_6)$alkanoyl, $(C_1\text{-}C_6)$alkoxycarbonyl, and $(C_2\text{-}C_6)$alkanoyloxy.

3. The complex of claim 1 or a solvate thereof, wherein the compound and the $Zn^{2+}$ are present in a ratio of about 2:1.

4. The complex or solvate of claim 1 which is charge neutral.

5. The complex of claim 1 which is a complex of formula (101):

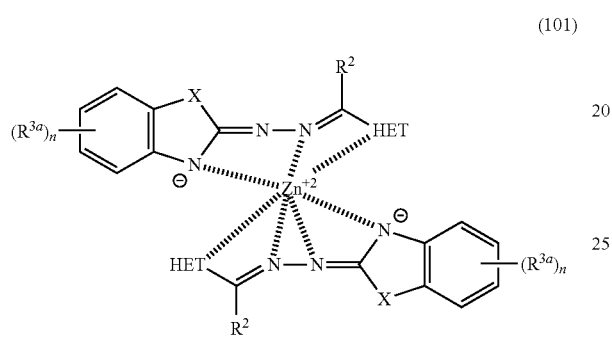

(101)

or a solvate thereof.

6. The complex of claim 1 or a solvate thereof wherein HET is selected from the group consisting of:

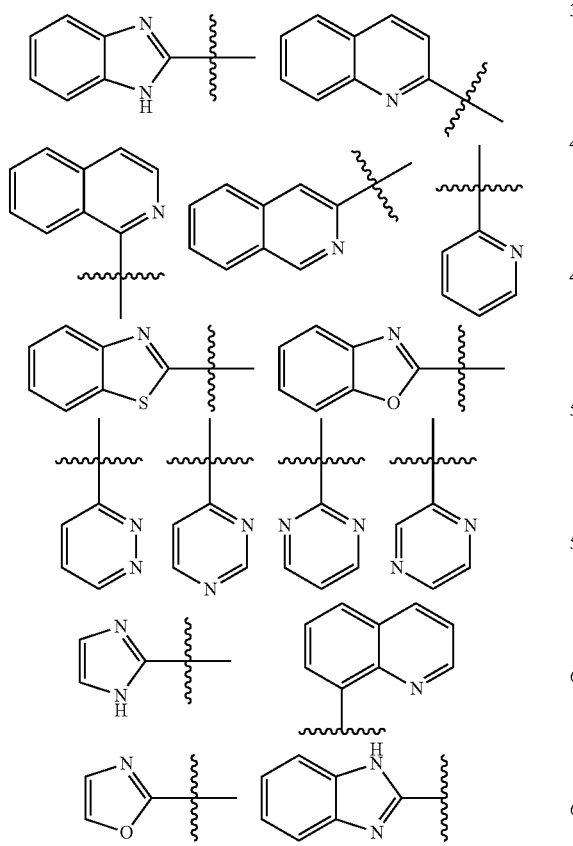

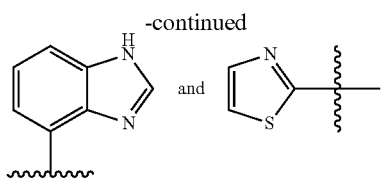

wherein HET is optionally substituted with one or more groups independently selected from $(C_1\text{-}C_6)$alkyl, $(C_2\text{-}C_6)$alkylaminocarbonyl and $(C_2\text{-}C_6)$alkanoylamino and $-N(R^a)_2$.

7. A neutral coordination complex comprising $Zn^{2+}$ and a compound selected from the group consisting of:

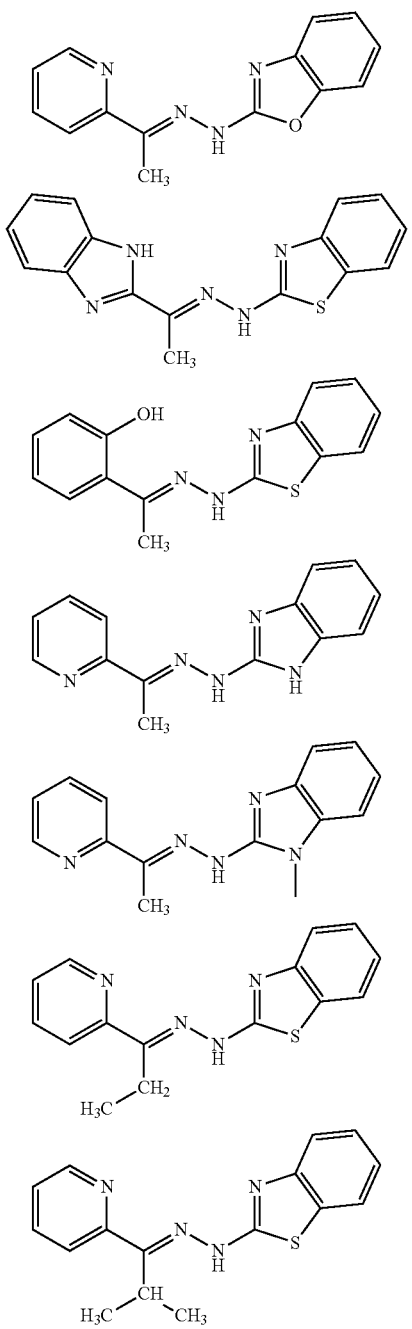

-continued

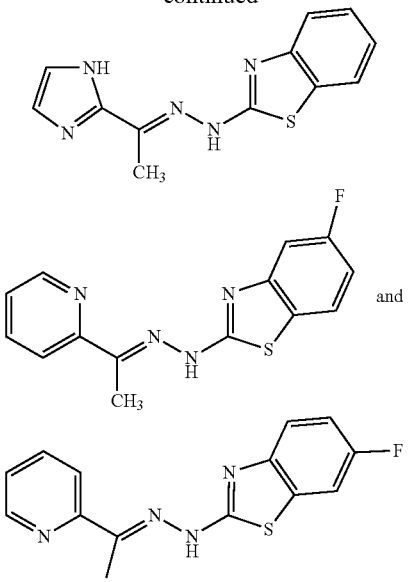

wherein the ratio of the compound to Zn²⁺ is about 2:1, or a solvate thereof.

8. The complex:

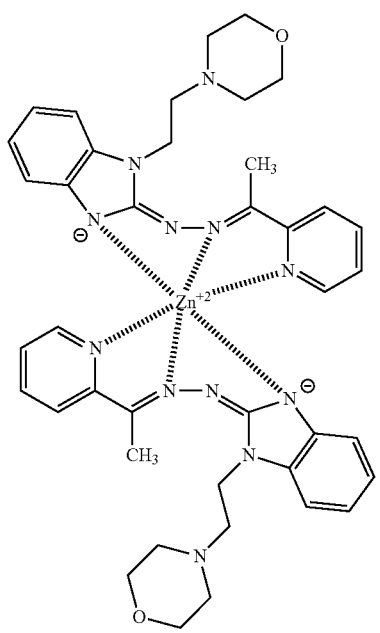

or a solvate thereof.

9. A pharmaceutical composition, comprising a complex of claim 1 or a solvate thereof, and a pharmaceutically acceptable carrier.

10. An injectable pharmaceutical formulation comprising, a complex of claim 1 or a solvate thereof, and a pharmaceutically acceptable carrier.

11. A pharmaceutical composition, which is formulated for administration by injection, comprising a pharmaceutically acceptable carrier and a complex comprising Zn²⁺ and a compound of formula (IIaa):

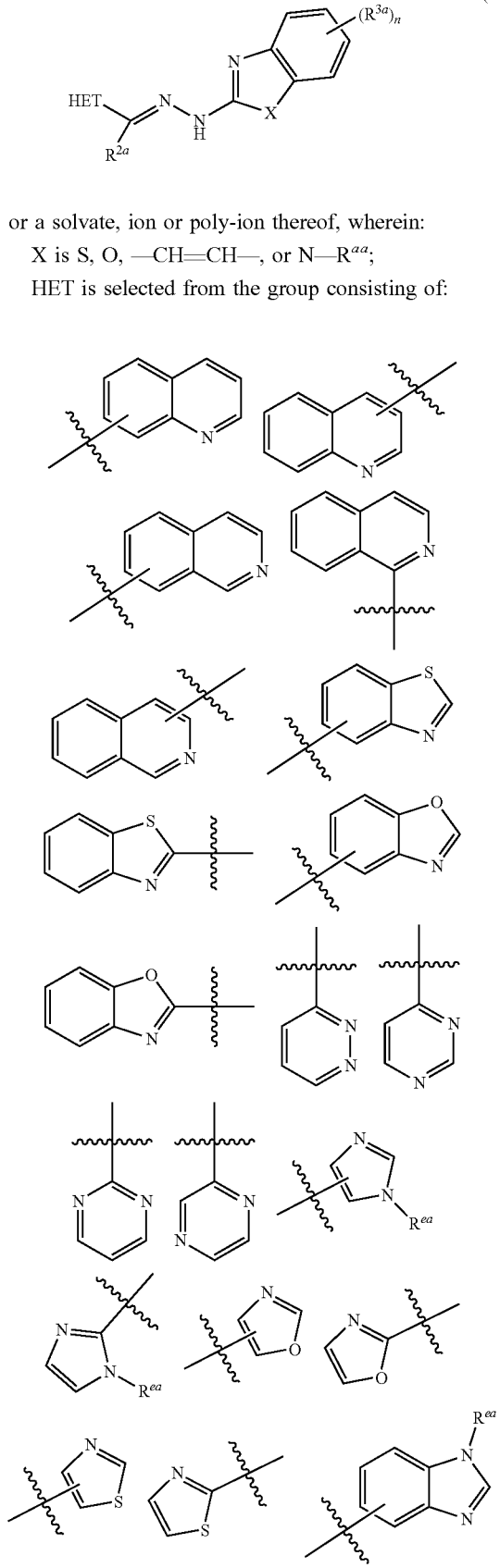

or a solvate, ion or poly-ion thereof, wherein:
X is S, O, —CH=CH—, or N—R$^{aa}$;
HET is selected from the group consisting of:

-continued

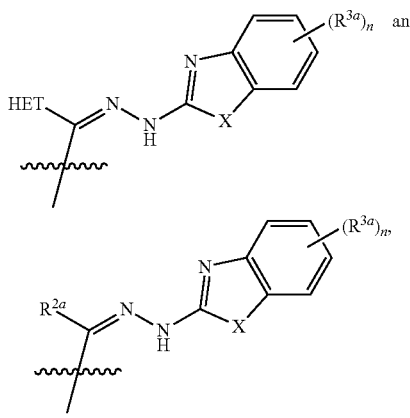

wherein HET is optionally substituted with one or more groups independently selected from halo, cyano, hydroxy, nitro, —N($R^{aa}$)$_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_1$-$C_6$)alkoxycarbonyl, ($C_2$-$C_6$)alkanoyloxy, wherein any phenyl, ($C_1$-$C_6$)alkyl, ($C_1$-$C_6$)alkoxy, ($C_2$-$C_6$)alkenyl, ($C_2$-$C_6$)alkynyl, and ($C_3$-$C_6$)cycloalkyl, is optionally substituted with one or more groups independently selected from halo, azido, cyano, hydroxy, nitro, —N($R^{ba}$)$_2$, carboxy, ($C_3$-$C_6$)cycloalkyl, ($C_1$-$C_6$)alkanoyl, ($C_1$-$C_6$)alkoxycarbonyl, ($C_2$-$C_6$)alkanoyloxy, and ($C_1$-$C_6$)alkoxy that is optionally substituted with carboxy;

each $R^{2a}$ is independently selected from the group consisting of H, phenyl, ($C_1$-$C_6$)alkyl, ($C_2$-$C_6$)alkenyl, ($C_2$-$C_6$)alkynyl, and ($C_3$-$C_6$)cycloalkyl, wherein any phenyl, ($C_1$-$C_6$)alkyl, ($C_2$-$C_6$)alkenyl, ($C_2$-$C_6$)alkynyl, and ($C_3$-$C_6$)cycloalkyl, is optionally substituted with one or more groups independently selected from halo, —N($R^{ca}$)$_2$, ($C_3$-$C_6$)cycloalkyl, ($C_1$-$C_6$)alkoxy, and ($C_2$-$C_6$)alkanoyloxy;

n is 0, 1, 2, 3, or 4;

each $R^{3a}$ is independently selected from halo, cyano, hydroxy, nitro, —N($R^{da}$)$_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy, wherein any phenyl, ($C_1$-$C_6$)alkyl, ($C_2$-$C_6$)alkenyl, ($C_2$-$C_6$)alkynyl, ($C_1$-$C_6$)alkoxy, and ($C_3$-$C_6$)cycloalkyl, is optionally substituted with one or more groups independently selected from halo, cyano, hydroxy, nitro, —N($R^c$)$_2$, carboxy, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy;

$R^{aa}$ is selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, —N($R^{ga}$)$_2$, morpholino, and ($C_1$-$C_6$)alkoxy; or two $R^{aa}$ taken together with the nitrogen to which they are attached form a azetidino, pyrrolidino, piperidino, or morpholino ring;

each $R^{ba}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, heteroaryl, and ($C_1$-$C_6$)alkoxy; or two $R^{ba}$ taken together with the nitrogen to which they are attached form a azetidino, pyrrolidino, piperidino, or morpholino ring; and each $R^{ca}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^{ca}$ taken together with the nitrogen to which they are attached form a azetidino, pyrrolidino, piperidino, or morpholino ring;

each $R^{da}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^{da}$ taken together with the nitrogen to which they are attached form a azetidino, pyrrolidino, piperidino, or morpholino ring; or a solvate thereof;

$R^{ea}$ is independently selected from the group consisting of H and ($C_1$-$C_6$)alkyl that is optionally substituted with one or more groups independently selected from halo, ($C_3$-$C_6$)cycloalkyl, —N($R^{fa}$)$_2$, and ($C_1$-$C_6$)alkoxy;

each $R^{fa}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^{fa}$ taken together with the nitrogen to which they are attached form a azetidino, pyrrolidino, piperidino, or morpholino ring; and each $R^{ga}$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, $(C_3-C_6)$ cycloalkyl, and $(C_1-C_6)$alkoxy; or two $R^{ga}$ taken together with the nitrogen to which they are attached form a azetidino, pyrrolidino, piperidino, or morpholino ring; and wherein the ratio of the compound to $Zn^{2+}$ is about 2:1.

12. A pharmaceutical composition, comprising a pharmaceutically acceptable carrier and the complex:

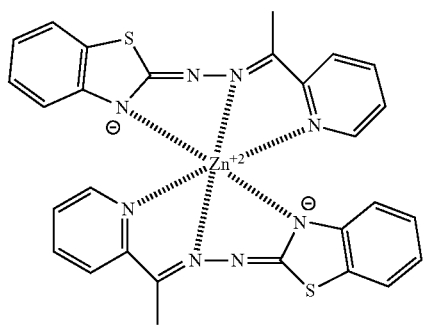

or a solvate thereof.

13. The complex of claim 1 wherein n is 0.

* * * * *

UNITED STATES PATENT AND TRADEMARK OFFICE
CERTIFICATE OF CORRECTION

PATENT NO. : 10,729,671 B2
APPLICATION NO. : 15/545975
DATED : August 4, 2020
INVENTOR(S) : David J. Augeri et al.

It is certified that error appears in the above-identified patent and that said Letters Patent is hereby corrected as shown below:

In the Claims

Column 24, Line 55, Claim 1, please delete "and" and insert -- , --;

Column 27, Lines 18-28, Claim 5, please delete the following compound:

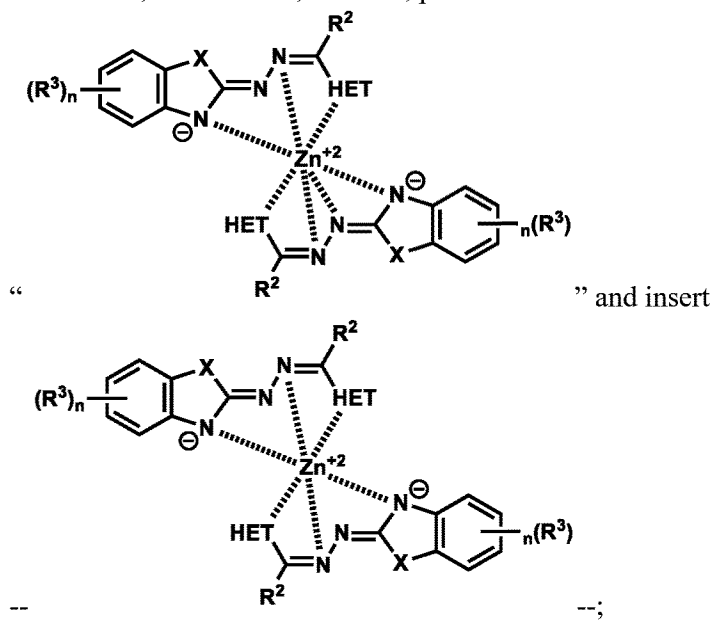

" and insert

-- ... --;

Column 33, Line 8, Claim 39, please delete "A pharmaceutical composition, comprising a pharmaceutically acceptable carrier and the complex" and insert -- A pharmaceutical composition, which is formulated for administration by injection, comprising a pharmaceutically acceptable carrier and the complex -- therefor.

Signed and Sealed this
Fourth Day of May, 2021

Drew Hirshfeld
*Performing the Functions and Duties of the
Under Secretary of Commerce for Intellectual Property and
Director of the United States Patent and Trademark Office*